(12) United States Patent
Kang et al.

(10) Patent No.: US 9,901,511 B2
(45) Date of Patent: Feb. 27, 2018

(54) INTELLIGENT MASSAGE BATHING SYSTEM AND METHOD FOR CONTROLLING THE SAME

(71) Applicant: Dartpoint Tech. Co., Ltd., Taipei (TW)

(72) Inventors: Chi-Lin Kang, New Taipei (TW); Chung-Hsin Hsieh, Taipei (TW); Chao-Yuan Huang, Taipei (TW)

(73) Assignee: DARTPOINT TECH CO., LTD., Taipei (TW)

( * ) Notice: Subject to any disclaimer, the term of this patent is extended or adjusted under 35 U.S.C. 154(b) by 141 days.

(21) Appl. No.: 14/721,003

(22) Filed: May 26, 2015

(65) Prior Publication Data

US 2015/0335523 A1 Nov. 26, 2015

Related U.S. Application Data

(60) Provisional application No. 62/002,946, filed on May 26, 2014.

(30) Foreign Application Priority Data

Oct. 16, 2014 (TW) .............................. 103135864 A

(51) Int. Cl.
*A61H 33/00* (2006.01)
*G06F 19/00* (2018.01)
*A61H 23/02* (2006.01)

(52) U.S. Cl.
CPC ....... *A61H 33/005* (2013.01); *A61H 33/0087* (2013.01); *G06F 19/3481* (2013.01);
(Continued)

(58) Field of Classification Search
CPC .............. A61H 33/005; A61H 33/0087; A61H 2033/0058; A61H 2033/0079;
(Continued)

(56) References Cited

U.S. PATENT DOCUMENTS 5,086,385 A * 2/1992 Launey ............... G06F 3/04847
340/6.11
6,407,469 B1 * 6/2002 Cline .................... A61H 33/005
307/11
(Continued)

FOREIGN PATENT DOCUMENTS

TW 201023806 7/2010
TW 397572 2/2011

*Primary Examiner* — J. Casimer Jacyna
(74) *Attorney, Agent, or Firm* — Mark M. Friedman

(57) ABSTRACT

An intelligent massage bathing system applied for a massage bathing equipment is disclosed herein, which comprises a plurality of attached devices, a massage bathing control unit, an operating panel unit and a master control device. The attached devices includes at least one first attached devices and at least one second attached devices, wherein the at least one first attached devices is configured as at least one slave control device. The master control device establishes a master-slave connection with the at least one slave control device, and commands to directly control the at least one slave control device to actuate relatively to the massage bathing equipment, according to an instruction generated from the operating panel unit.

32 Claims, 33 Drawing Sheets

(52) U.S. Cl.
CPC .. *A61H 23/0245* (2013.01); *A61H 2033/0054* (2013.01); *A61H 2033/0058* (2013.01); *A61H 2033/0079* (2013.01); *A61H 2201/0207* (2013.01); *A61H 2201/10* (2013.01); *A61H 2201/5015* (2013.01); *A61H 2201/5035* (2013.01); *A61H 2201/5043* (2013.01); *A61H 2201/5058* (2013.01); *A61H 2201/5097* (2013.01)

(58) Field of Classification Search
CPC .... A61H 2201/5097; A61H 2204/5043; A61H 2201/5015; A61H 2201/10; A61H 2201/5035; A61H 2201/5007
See application file for complete search history.

(56) References Cited

U.S. PATENT DOCUMENTS 8,280,535 B2 * 10/2012 Hsieh ................... G05B 19/042
307/11
2011/0046796 A1 2/2011 Brochu et al.

\* cited by examiner

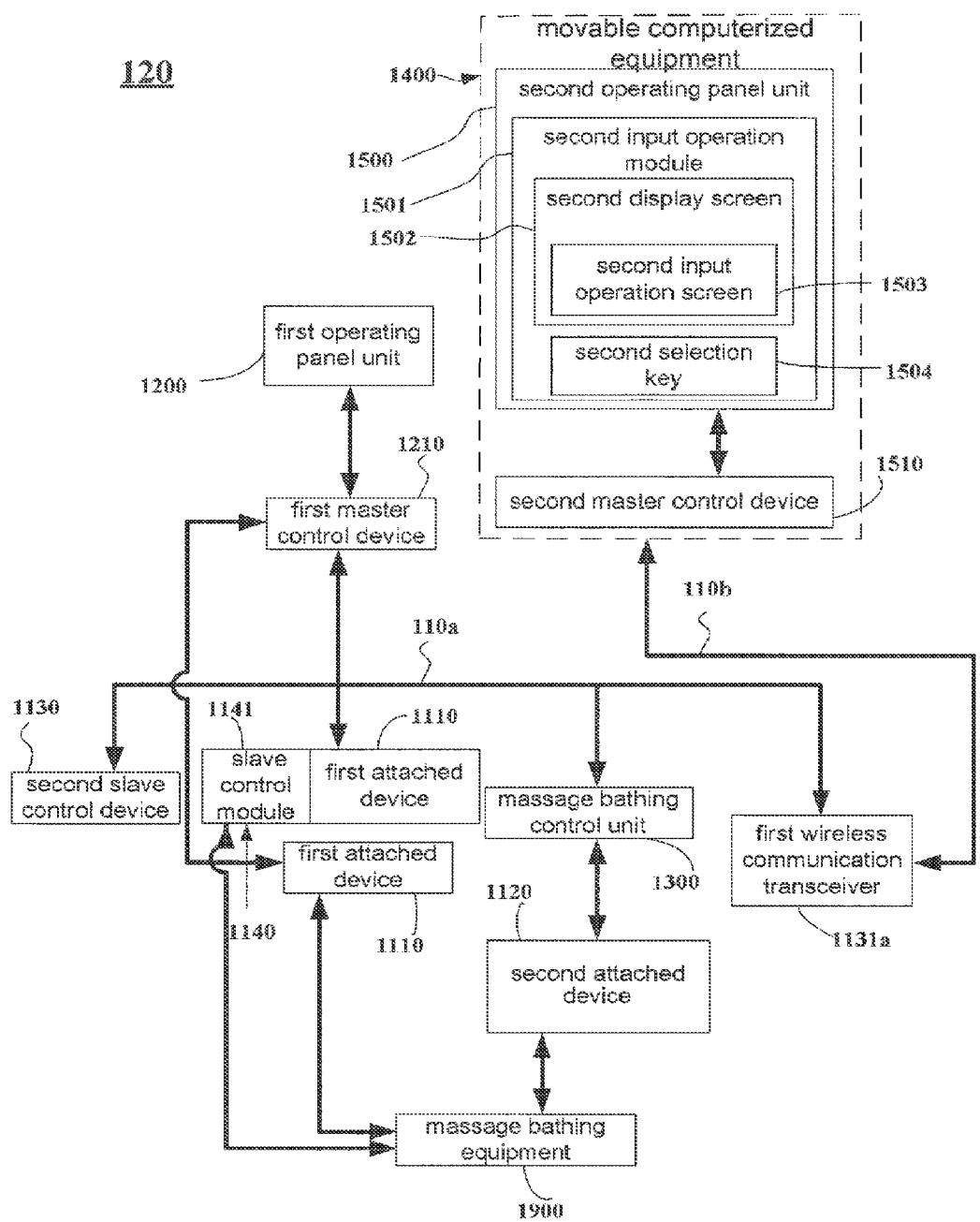
Fig. 11-a

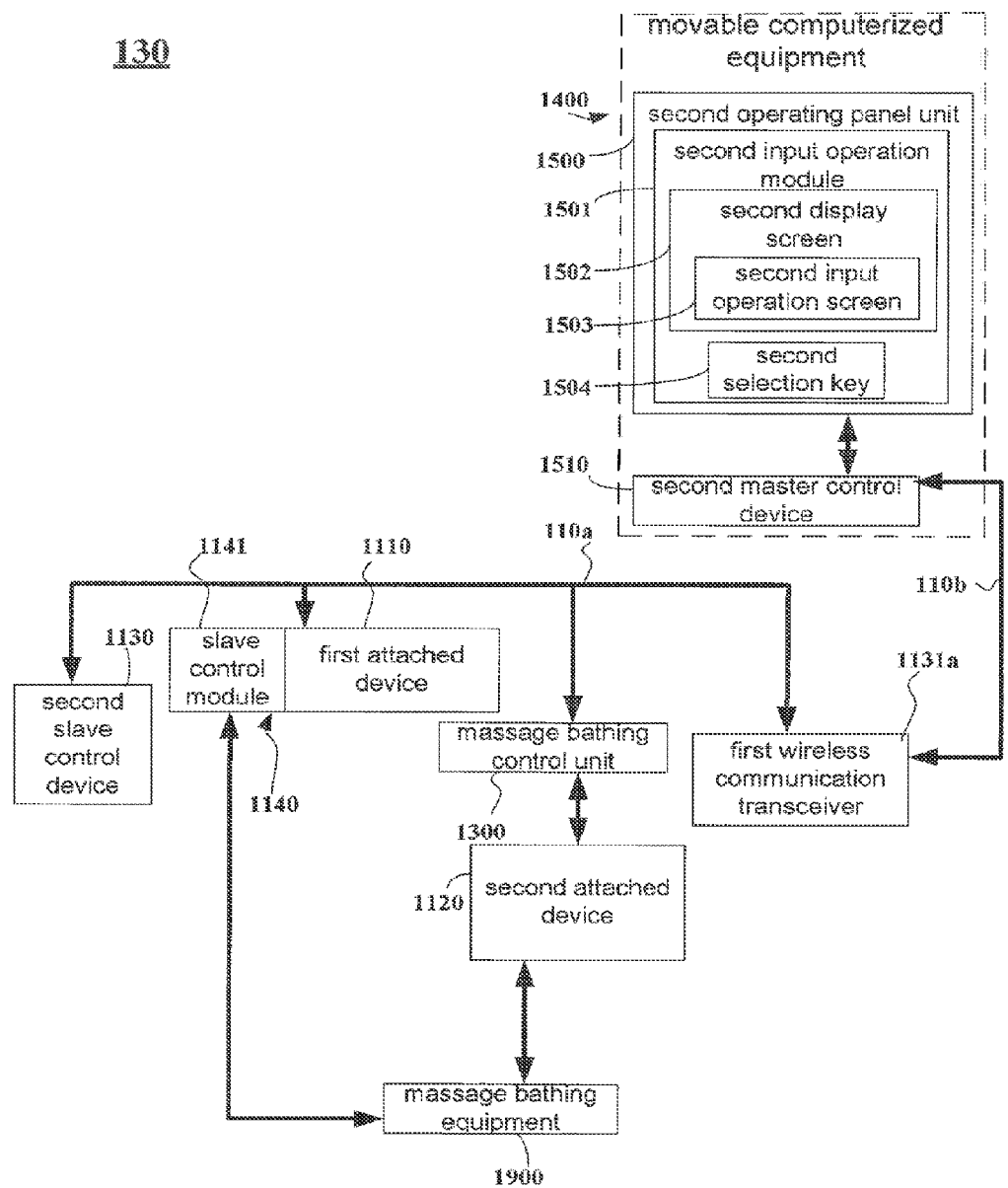
Fig. 11-b

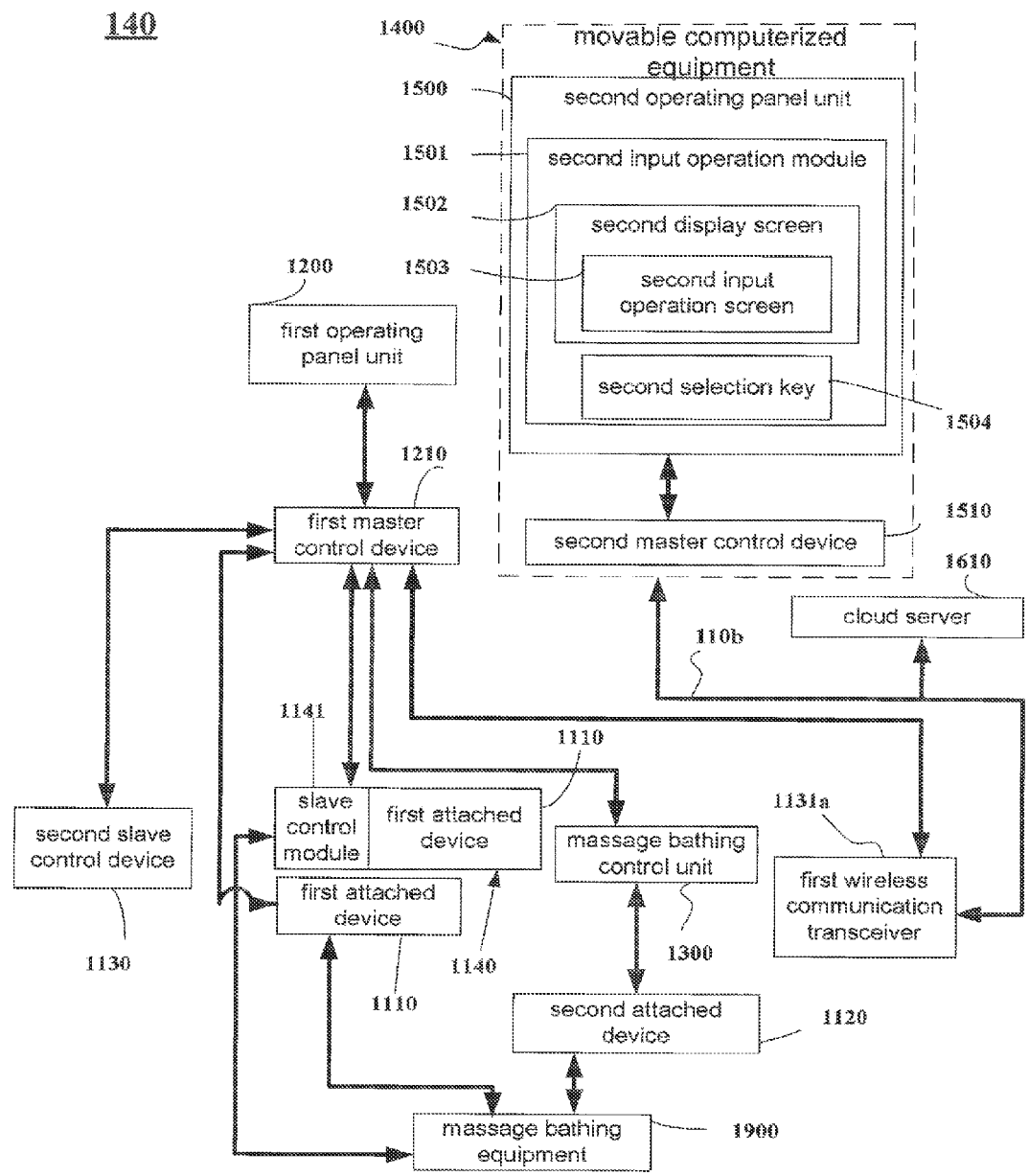
Fig. 12-a

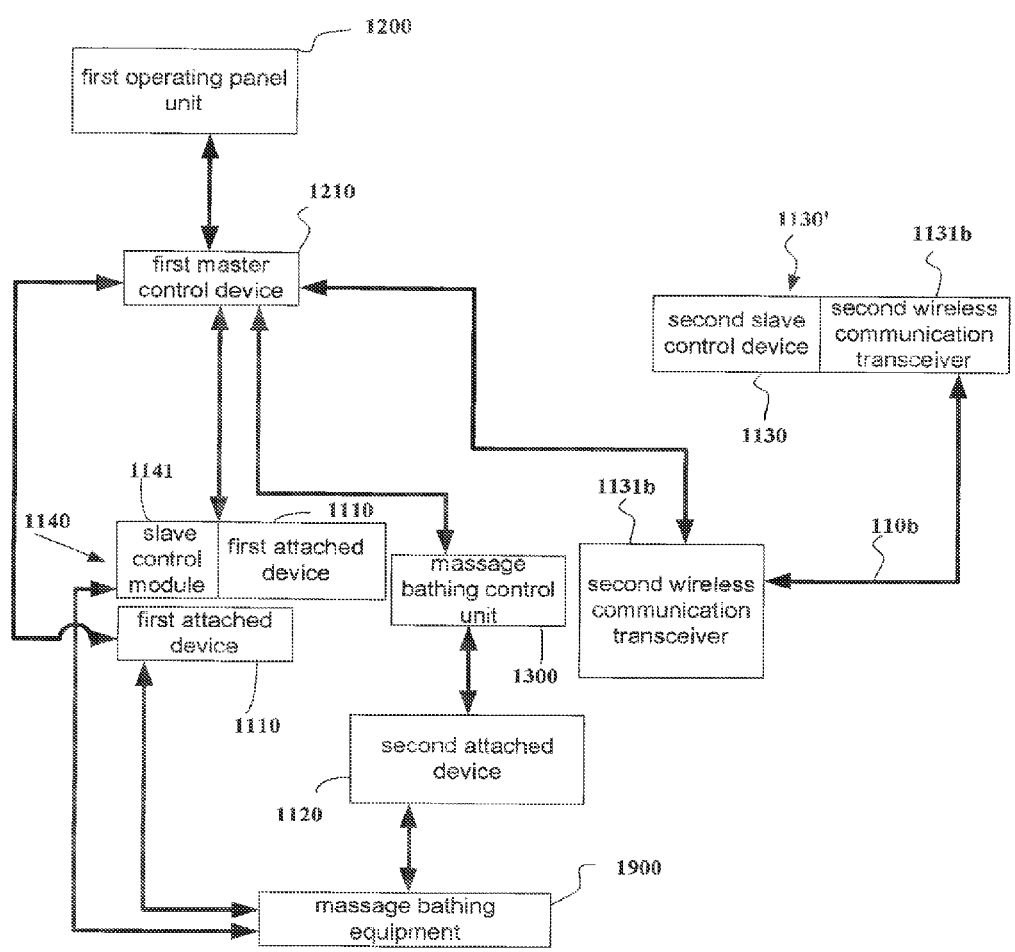
Fig. 12-b

S01 — inputting an instruction on a display screen through an input operation module of an operating panel unit, wherein the display screen is configured to selectively display an actuated state of one or a combination of several of attached devices relatively to the massage bathing equipment, and the attached devices includes at least one first attached device and at least one second attached device, wherein the at least one first attached device is configured as the at least one first slave control device, and a massage bathing control unit controls the actuation of the at least one second attached device S02 — configuring a master control device for directly controlling, through establishing a master-slave connection, on the at least one first slave control device, so that the master control device commands to directly control an actuation of the at least one first slave control device relatively to the massage bathing equipment, according to the instruction from the operating panel unit

Fig. 31

INTELLIGENT MASSAGE BATHING SYSTEM AND METHOD FOR CONTROLLING THE SAME

CROSS-REFERENCE TO RELATED APPLICATIONS

This application claims the benefit of U.S. Provisional Application No. 62/002,946, filed on May 26, 2014, which is hereby incorporated by reference for all purposes as if fully set forth herein.

FIELD OF THE INVENTION

The present invention relates to an intelligent massage bathing system and method for controlling the same, and in particularly related to the technical field of massage bathing equipment such as massage bathtub/hot tub, SPA pool or swimming pool.

BACKGROUND OF THE INVENTION

Currently, it is widely popular for the families or leisure places in the United States and Europe to install a massage bathing equipment such as massage bathtub/hot tub, SPA pool or swimming pool. It is essential to perform an input/output analog control by a traditional SPA controller on a variety of attached devices, such as motors, air valves, heaters and so on, connected to the massage bathing equipment, peripherally. However, those conventional massage bathing systems exist a number of potential problems, namely except that the conventional massage bathing system only can be fixed by replacing the same components properly while a general periodically maintenance or an unexpected failure, the conventional massage bathing system cannot provide easy installation of extra hardware expansion kits, upgrading, or internet application, without replacing the software and hardware of the SPA controller. Therefore, a user cannot easily install the popular 3C electronic product, the video/audio entertainment equipment or other additional equipment not applicable to the massage bathing system. Moreover, the conventional massage bathing system is very expensive, and even if the user has an idea to expand the conventional massage bathing system, the idea cannot be achieved, easily.

Furthermore, those devices in the conventional massage bathing system lack mutually controlling/communication function. This greatly reduces the possibility of increasing installations of the additional attached devices for users.

As referring to the FIG. 1, FIG. 1 is an architectural schematic view of the first conventional massage bathing system. The first conventional massage bathing system 10 comprises a SPA controller 11 and a panel 12. The panel 12 is a passive panel. A user can operate on the SPA controller 11 through the panel 12 for controlling the attached devices peripherally connected to the massage bathing equipment. However, when the user wants to increasingly install the additional devices, there is a need to ask the manufacturer to redesign the SPA controller 11 so that the massage bathing system cannot be expanded, simply. Thus, this will invoke a lot of inconvenience in usage thereof.

Additionally referring to the FIG. 2, FIG. 2 is an architectural schematic view of the second conventional massage bathing system. The difference with the previous conventional massage bathing system is that: a panel 22 of the second conventional massage bathing system 20 is a human machine interface design. The user can individually controls a single attached device connected to the massage bathing equipment by clicking a single button of the panel 22 via the SPA controller 21.

Additionally referring to the FIG. 3, FIG. 3 is an architectural schematic view of the third conventional massage bathing system. The difference with the previous conventional massage bathing system is that the third conventional massage bathing system 30 further comprises a Wi-Fi module 33. The user can send a remote control command to the Wi-Fi module 33 by a remote control device (such as a mobile phone or a tablet) and individually controls the single attached device connected to the massage bathing equipment via a SPA controller 31. An operation result of the attached device can be displayed on a panel 32. However, the remote control device cannot control other devices electrically connected to the panel 32 and cannot use the functions thereof such as the internet. As the aforementioned three conventional massage bathing systems are required to modify their microprocessor of the SPA controller to add/expand the attached devices therein, the users and the manufacturers are very inconvenient.

With the technological advances and the needs of users, recently, more and more users request to add 3C electronic product to the conventional massage bathing system. It's difficult to add 3C electronic product to the conventional massage bathing system, due to the conventional massage bathing system principally consists of a control panel and a SPA controller. The control panel is used by the user to input a single instruction for controlling the SPA controller. Then, the SPA controller controls action of each corresponding attached device such as a blower, an air valve, a pump or a heater according to the single instruction. That causes that the control panel cannot control those attached devices directly. Therefore, in order to add the additional functions of the SPA controller, it is necessary for the user to spend a lot of time in redesigning the SPA controller. Thus, there is a need to solve the problems of simplifying the method of expanding functions of the SPA controller and improve the mutual controls among the devices.

SUMMARY OF THE INVENTION

In order to solve the aforementioned drawbacks of the prior art, an objective of the present invention is to provide an intelligent massage bathing system, which can directly control a plurality of slave control devices by a master-slave connection architecture established between a master control device and the plurality of slave control devices. Furthermore, the problems of expanding functions and the mutual controls among the devices, derived from the conventional massage bathing system, can be solved.

To achieve the above objectives, the present invention provides an intelligent massage bathing system applied for a massage bathing equipment. The intelligent massage bathing system comprises a plurality of attached devices, a massage bathing control unit, a first operating panel unit and a first master control device.

The attached devices are provided for directly actuating relatively to the massage bathing equipment, which includes at least one first attached device and at least one second attached device, wherein the at least one first attached device is configured as at least one first slave control device.

The massage bathing control unit is configured for controlling an actuation of the at least one second attached device.

The first operating panel unit includes a first display screen and a first input operation module for inputting an instruction on the first display screen, the first display screen is configured to selectively display an actuated state of one or a combination of several of the attached devices.

The first master control device is electrically connected with the first operating panel unit and directly controlling, through establishing a master-slave connection, on the at least one first slave control device, so that the first master device commands to directly control the at least one first slave control device to actuate relatively to the massage bathing equipment, according to the instruction from the first operating panel unit.

In a preferred embodiment, the at least one first attached device further comprises one or a combination of several of a jet schedule controlling device, an automatic water replenishing device, an infrared device, a photography device and an ultrasonic device, and the at least one second attached device further comprises one or a combination of several of a blower, a motor, an air valve, a sensor, a pump, an internal light controlling device and a heater.

In a preferred embodiment, the intelligent massage bathing system further comprises a plurality of second slave control devices, each of which establishes a master-slave connection with the first master control device respectively for actuating with direct control of the first master control device, the first display screen is configured to selectively display an actuated state of one or a combination of several of the attached devices and the second slave control devices.

In a preferred embodiment, the second slave control devices comprises at least one wireless communication transceiver, the other second slave control devices comprises one or a combination of several of an external lighting control device, a media player device, an internet device, an external storage device and a voice/music device.

In a preferred embodiment, the at least one wireless communication transceiver comprises at least one first wireless communication transceiver.

In a preferred embodiment, the intelligent massage bathing system further comprises a data bus network architecture which comprises a first region master node and a plurality of first region slave nodes for electrically connecting with the first region master node, wherein a portion of the at least one first slave control device and/or a portion of the second slave control devices are respectively disposed on the first region slave nodes, and the first master control device is disposed on the first region master node.

In a preferred embodiment, the first wireless communication transceiver is disposed on the corresponding first region slave node.

In a preferred embodiment, the data bus network architecture comprises one or a combination of several of RS-485, CAN Bus and LIN Bus.

In a preferred embodiment, the intelligent massage bathing system further comprises a wireless communication network architecture, a second operating panel unit and a second master control device.

In a preferred embodiment, the wireless communication network architecture comprises a second region master node and at least one second region slave node for electrically connecting with the second region master node.

In a preferred embodiment, the second operating panel unit includes a second display screen and a second input operation module for inputting an instruction on the second display screen, the second display screen is configured to selectively display an actuated state of one or a combination of several of the attached devices and the second slave control devices. The second master control device disposed on the second region master node and electrically connecting with the second operating panel unit, wherein the first wireless communication transceiver is disposed on the at least one second region slave node.

In a preferred embodiment, when the at least one wireless communication transceiver is also correspondingly disposed on the first region slave node, the second master control device commands to directly control the actuation of the corresponding at least one first slave control device and/or the other second slave control devices, via the wireless communication transceiver, according to the instruction from the second operating panel unit.

In a preferred embodiment, the second master control device further commands one or several of actuation of the at least one second attached device controlled through the massage bathing control unit, actuation of the at least one first slave control device and actuations of the other second slave control devices, via the first wireless communication transceiver, according to the instruction from the second operating panel unit.

In a preferred embodiment, the at least one wireless communication transceiver further comprises at least one second wireless communication transceiver which comprises one or a combination of several of a Zigbee transceiver, a RF transceiver and a Bluetooth transceiver.

In a preferred embodiment, the second wireless communication transceiver is disposed on another corresponding first region slave node.

In a preferred embodiment, the second master control device further commands one or several of actuation of the at least one second attached device controlled through the massage bathing control unit, and actuations of the other second slave control devices, via the first wireless communication transceiver and the second wireless communication transceiver, according to the instruction from the second operating panel unit.

In a preferred embodiment, the first master control device further commands one or several of actuation of the at least one second attached device controlled through the massage bathing control unit, and actuation of the at least one of the remaining second slave control devices, via the second wireless communication transceiver, according to the instruction from the first operating panel unit.

In a preferred embodiment, at least one of the massage bathing control unit and the first operating panel unit are configured as one of the second slave control devices.

In a preferred embodiment, one of the massage bathing control unit and the first operating panel unit is integrally assembled with the first master control device.

In a preferred embodiment, one of the at least one first attached device and the at least one second slave control devices is integrally assembled with the first master control device.

In a preferred embodiment, the first master control device comprises a memory unit, a network communication interface unit, a general asynchronous transceiver unit, a microprocessor unit, the microprocessor unit comprises a plurality of drive control components and a multitasking kernel, the drive control components are configured to process a direct control, through a master-slave connection, on the at least one first slave control device and the second slave control devices.

In a preferred embodiment, the multitasking kernel comprises multi-threads.

In a preferred embodiment, the first master control device further comprises an image processing unit, a voice processing unit, an information collection unit, an output controlling unit, a USB interface and a power management unit.

In a preferred embodiment, the at least one first slave control device further comprises a slave control module.

To achieve the above objectives, the present invention provides another intelligent massage bathing system applied for a massage bathing equipment. The intelligent massage bathing system comprises a plurality of attached devices, a massage bathing control unit, a wireless communication network architecture, an operating panel unit and a master control device.

In a preferred embodiment, the attached devices includes at least one first attached device and at least one second attached device, wherein the at least one first attached device is configured as at least one first slave control device.

In a preferred embodiment, the massage bathing control unit is configured for controlling an actuation of the at least one second attached device.

In a preferred embodiment, the wireless communication network architecture comprises a master node and at least one slave node for connecting with the master node.

In a preferred embodiment, the operating panel unit includes a display screen and an input operation module for inputting an instruction on the display screen.

In a preferred embodiment, the master control device is provided for electrically connecting with the operating panel unit and being disposed on the master node, and for directly controlling, through establishing a master-slave connection, on the at least one first slave control device.

In a preferred embodiment, the intelligent massage bathing system further comprises at least one second slave control device for establishing the master-slave connection with the master control device to actuate with direct control of the master control device, the at least one second slave control device comprises at least one wireless communication transceiver disposed on the at least one slave node. The master control device commands to directly control an actuation of the at least one first slave control device and/or the at least one of the remaining second slave control devices via the wireless communication network architecture, according to the instruction from the operating panel unit, and the display screen is configured to selectively display an actuated state of one or a combination of several of the attached devices and the at least one second slave control device.

In a preferred embodiment, the at least one wireless communication transceiver comprises one or a combination of several of a Wi-Fi transceiver, a Zigbee transceiver, a RF transceiver and a Bluetooth transceiver.

In a preferred embodiment, the intelligent massage bathing system further comprises a data bus network architecture which is respectively connected to the at least one wireless communication transceiver, a portion of the at least one first slave control device and/or a portion of the at least one second slave control device.

In a preferred embodiment, the master control device directly commands one or several of actuation of the at least one second attached device controlled through the massage bathing control unit, actuation of the at least one first slave control device and actuations of the other at least one second slave control devices, via the wireless communication transceiver, according to the instruction from the operating panel unit.

In a preferred embodiment, the master control device and the operating panel unit are disposed in a movable computerized equipment, the master control device comprises a memory unit, a network communication interface unit, a microprocessor unit, a program code for generating an inputting operation screen and a plurality of programmable drive control components for directly controlling, through establishing a master-slave connection, on the at least one first slave control device and the at least one second slave control device.

In a preferred embodiment, the intelligent massage bathing system further comprises a cloud server connected to the wireless communication network architecture for providing the program codes for generating an inputting operation screen and a plurality of programmable drive control components for loading into the master control device.

In a preferred embodiment, the data bus network architecture comprises one or a combination of several of RS-485, CAN Bus and LIN Bus.

To achieve the above objectives, the present invention provides a controlling method of an intelligent massage bathing system applied for a massage bathing equipment.

The controlling method comprises the following steps of:

first, inputting an instruction on a display screen through an input operation module of an operating panel unit, wherein the display screen is configured to selectively display an actuated state of one or a combination of several of attached devices relatively to the massage bathing equipment, and the attached devices includes at least one first attached device and at least one second attached device, wherein the at least one first attached device is configured as the at least one first slave control device, and a massage bathing control unit controls the actuation of the at least one second attached device; and configuring a master control device for directly controlling, through establishing a master-slave connection, on the at least one first slave control device, so that the master control device commands to directly control an actuation of the at least one first slave control device relatively to the massage bathing equipment, according to the instruction from the operating panel unit.

In a preferred embodiment, the master control device is configured to process a direct control, through a master-slave connection, on the at least one second slave control device, wherein the display screen is configured to selectively display one or several of actuated state of the at least one second slave control device.

In a preferred embodiment, the at least one second slave control device comprises at least one wireless communication transceiver.

In a preferred embodiment, the controlling method comprises the step of making the master control device to be respectively connected to a portion of the at least one first slave control device and/or a portion of the at least one second slave control device via a data bus network architecture.

In a preferred embodiment, the controlling method further comprises the step of configuring the master control device to be connected with at least one wireless communication transceiver, via a wireless communication network architecture.

In a preferred embodiment, when the at least one wireless communication transceiver is also connected to the data bus network architecture, the master control device commands to directly control an actuation of the corresponding at least one first slave control device and/or the corresponding at least one second slave control device, via the at least one wireless communication transceiver, according to the instruction from the operating panel unit.

In a preferred embodiment, the controlling method further comprises the step of configuring the master control device to command one or several of actuation of the at least one second attached device controlled through the massage bathing control unit, actuation of the at least one first slave control device and actuation of the at least one of the remaining second slave control devices, via the wireless communication transceiver, according to the instruction from the operating panel unit.

In a preferred embodiment, at least one of the massage bathing control unit and the operating panel unit is configured as one of the at least one second slave control devices.

In a preferred embodiment, the intelligent massage bathing system comprises a data bus network architecture which comprises one or a combination of several of RS-485, CAN Bus and LIN Bus.

To achieve the above objectives, the present invention provides an intelligent massage bathing system applied for a massage bathing equipment, comprising: a plurality of attached devices, a massage bathing control unit, a first operating panel unit and a first master control device.

In a preferred embodiment, the attached devices are provided for directly actuating relatively to the massage bathing equipment.

In a preferred embodiment, the massage bathing control unit controls the actuations of a portion of the attached devices.

In a preferred embodiment, the first operating panel unit includes a first display screen and a first input operation module for inputting an instruction on the first display screen, the first display screen is configured to selectively display an actuated state of one or a combination of the attached devices.

In a preferred embodiment, the first master control device is used for electrically connecting with the first operating panel unit.

In a preferred embodiment, a plurality of slave control devices are respectively connected to the first master control device via a data bus network architecture, the first display screen is configured to selectively display an actuated state of one or a combination of several of the slave control devices, wherein a slave-slave connection is processed among the slave control devices for transmitting a message and/or directly controlling.

In a preferred embodiment, the attached devices include at least one first attached device and at least one second attached device, wherein the slave control devices include a plurality of second slave control devices, and at least one first slave control device configured with the at least one first attached device, the massage bathing control unit is configured to control an actuation of the at least one second attached device.

In a preferred embodiment, the at least one first attached device further comprises one or a combination of several of a jet schedule controlling device, an automatic water replenishing device, an infrared device, a photography device and an ultrasonic device, and the at least one second attached device further comprises one or a combination of several of a blower, a motor, an air valve, a sensor, a pump, an internal light controlling device and a heater.

In a preferred embodiment, the intelligent massage bathing system further comprises a plurality of second slave control devices respectively connected to each of the first slave control device for processing a slave-slave connection and actuation. The first display screen is configured to selectively display the actuated state of one or a combination of several of the at least one first attached device and the second slave control devices.

In a preferred embodiment, the second slave control devices comprises at least one wireless communication transceiver, the other second slave control devices comprises one or a combination of an external lighting control device, a media player device, an internet device, an external storage device and a voice/music device.

In a preferred embodiment, the at least one wireless communication transceiver comprises at least one first wireless communication transceiver.

In a preferred embodiment, the intelligent massage bathing system further comprises a data bus network architecture, the data bus network architecture comprises a first region master node and a plurality of first region slave nodes for electrically connecting with the first region master node, a portion of the at least one first slave control device and/or a portion of the second slave control devices are respectively disposed on the first region slave nodes, the first master control device is disposed on the first region master node.

In a preferred embodiment, the first wireless communication transceiver is disposed on the corresponding first region slave node.

In a preferred embodiment, the intelligent massage bathing system further comprises a wireless communication network architecture a second operating panel unit and a second master control device.

In a preferred embodiment, the wireless communication network architecture comprises a second region master node and at least one second region slave nodes for electrically connecting with the second region master node.

In a preferred embodiment, the second operating panel unit includes a second display screen and a second input operation module for inputting an instruction on the second display screen, the second display screen is configured to selectively display an actuated state of one or a combination of the attached devices and the second slave control devices.

In a preferred embodiment, the second master control device is disposed on the second region master node and is provided for electrically connecting with the second operating panel unit, the at least one wireless communication transceiver is disposed on the at least one second region slave node.

In a preferred embodiment, the second master control device further commands one or several of actuation of the at least one second attached device controlled through the massage bathing control unit, actuation of the at least one first slave control device and actuations of the other second slave control devices, via the first wireless communication transceiver, according to the instruction from the second operating panel unit.

In a preferred embodiment, the at least one wireless communication transceiver further comprises at least one second wireless communication transceiver which comprises one or a combination of several of a Zigbee transceiver, a RF transceiver and a Bluetooth transceiver.

In a preferred embodiment, the second wireless communication transceiver is disposed on another corresponding first region slave node.

In a preferred embodiment, the second master control device commands one or several of actuation of the at least one second attached device controlled through the massage bathing control unit and actuations of the other second slave control devices, via the first wireless communication transceiver and the second wireless communication transceiver, according to the instruction from the second operating panel unit.

In a preferred embodiment, the first master control device commands one or a plurality of actuation of the at least one second attached device controlled through the massage bathing control unit and actuation of the at least one of the remaining second slave control devices, via the second wireless communication transceiver, according to the instruction from the first operating panel unit.

In a preferred embodiment, at least one of the massage bathing control unit and the first operating panel unit are configured as one of the second slave control devices.

In a preferred embodiment, one of the massage bathing control unit and the first operating panel unit is integrally assembled with the first master control device.

In a preferred embodiment, one of the at least one first attached device and the second slave control device is integrally assembled with the first master control device.

In a preferred embodiment, the first master control device comprises a memory unit, a network communication interface unit, a general asynchronous transceiver unit, a microprocessor unit, the microprocessor unit comprises a plurality of drive control components and a multitasking kernel, the drive control components are configured to process a direct control, through a master-slave connection, on the first slave control device and the second slave control device.

In a preferred embodiment, the multitasking kernel comprises multi-threads.

In a preferred embodiment, the first master control device further comprises an image processing unit, a voice processing unit, an information collection unit, an output controlling unit, a USB interface and a power management unit.

In a preferred embodiment, the at least one first slave control device further comprises a slave control module.

In a preferred embodiment, the intelligent massage bathing system further comprises a data bus network architecture which comprises one or a combination of several of RS-485, CAN Bus and LIN Bus.

To achieve the above objectives, the present invention provides an intelligent massage bathing system applied for a massage bathing equipment, comprising: a plurality of attached devices, a massage bathing control unit, a first operating panel unit and a first a master control device.

In a preferred embodiment, the attached devices are provided for directly actuating relatively to the massage bathing equipment.

In a preferred embodiment, the massage bathing control unit is configured for controlling the actuations of a plurality of attached devices.

In a preferred embodiment, the first operating panel unit includes a first display screen and a first input operation module for inputting an instruction on the first display screen, the first display screen is configured to selectively display an actuated state of one or a combination of several of the attached devices.

In a preferred embodiment, the first master control device is used for electrically connecting with the first operating panel unit. The slave control devices are respectively connected to the first master control device via a data bus network architecture, the first display screen is configured to selectively display an actuated state of one or a combination of the slave control devices, wherein a slave-slave connection is processed between the slave control devices for transmitting a message and/or directly controlling.

In a preferred embodiment, the attached devices include at least one first attached device and at least one second attached device. The slave control devices include at least one first slave control device configured with the at least one first attached device and a plurality of second slave control devices, and the massage bathing control unit is configured to control an actuation of the at least one second attached device.

In a preferred embodiment, the at least one first attached device further comprises one or a combination of several of a jet schedule controlling device, an automatic water replenishing device, an infrared device, a photography device and an ultrasonic device, the at least one second attached device further comprises one or a combination of several of a blower, a motor, an air valve, a sensor, a pump, an internal light controlling device and a heater.

In a preferred embodiment, the intelligent massage bathing system further comprises a plurality of second slave control devices, each of which establishes a master-slave connection with the first master control device respectively for actuating by direct control of the first master control device, the first display screen is configured to selectively display an actuated state of one or a combination of the attached devices and the second slave control devices.

In a preferred embodiment, the second slave control devices comprises at least one wireless communication transceiver, the other second slave control devices comprises one or a combination of several of an external lighting control device, a media player device, an Internet device, an external storage device and a voice/music device.

In a preferred embodiment, the at least one wireless communication transceiver comprises at least one first wireless communication transceiver.

In a preferred embodiment, the data bus network architecture comprises a first region master node and a plurality of first region slave nodes for electrically connecting with the first region master node, a portion of the at least one first slave control device and/or a portion of the second slave control devices are respectively disposed on the first region slave nodes, the first master control device is disposed on the first region master node.

In a preferred embodiment, the first wireless communication transceiver is disposed on the corresponding first region slave node.

In a preferred embodiment, the massage bathing system further comprises a second operating panel unit and a second master control device.

In a preferred embodiment, the wireless communication network architecture comprises a second region master node and at least one second region slave node for connecting with the second region master node.

In a preferred embodiment, the second operating panel unit includes a second display screen and a second input operation module for inputting an instruction on the second display screen, the second display screen is configured to selectively display an actuated state of one or a combination of the attached devices and the second slave control devices.

In a preferred embodiment, the second master control device is disposed on the second region master node and electrically connect with the second operating panel unit, the first wireless communication transceiver is disposed on the at least one second region slave node.

In a preferred embodiment, when the at least one wireless communication transceiver also is disposed on the corresponding first region slave node, the second master control device commands to directly control an actuation of the at least one corresponding first slave control device and/or the other second slave control devices, via the wireless communication transceiver, according to the instruction from the second operating panel unit.

In a preferred embodiment, the second master control device commands one or several of actuation of the at least one second attached device controlled through the massage bathing control unit and actuations of the other second slave control devices, via the first wireless communication transceiver, according to the instruction from the second operating panel unit.

In a preferred embodiment, the at least one wireless communication transceiver further comprises at least one second wireless communication transceiver which comprises one or a combination of several of a Zigbee transceiver, a RF transceiver and a Bluetooth transceiver.

In a preferred embodiment, the second wireless communication transceiver is disposed on another corresponding first region slave node.

In a preferred embodiment, the second master control device further commands one or several of actuation of the at least one second attached device controlled through the massage bathing control unit and actuations of the other second slave control devices, via the first wireless communication transceiver and the second wireless communication transceiver, according to the instruction from the second operating panel unit.

In a preferred embodiment, the first master control device commands one or several of actuation of the at least one second attached device controlled through the massage bathing control unit and actuation of the at least one of the remaining second slave control devices, via the second wireless communication transceiver, according to the instruction from the first operating panel unit.

In a preferred embodiment, at least one of the massage bathing control unit and the first operating panel unit is configured as one of the second slave control devices.

In a preferred embodiment, one of the massage bathing control unit and the first operating panel unit is integrally assembled with the first master control device.

In a preferred embodiment, one of the at least one first attached device and the at least one second slave control device is integrally assembled with the first master control device.

In a preferred embodiment, the first master control device comprises a memory unit, a network communication interface unit, a general asynchronous transceiver unit, a microprocessor unit, the microprocessor unit comprises a plurality of drive control components and a multitasking kernel, the drive control components are configured to process a direct control, through a master-slave connection, on the at least one first slave control device and a plurality of second slave control devices.

In a preferred embodiment, the multitasking kernel comprises multi-threads.

In a preferred embodiment, the first master control device further comprises an image processing unit, a voice processing unit, an information collection unit, an output controlling unit, a USB interface and a power management unit.

In a preferred embodiment, the at least one first slave control device further comprises a slave control module.

In a preferred embodiment, the data bus network architecture comprises one or a combination of several of RS-485, CAN Bus and LIN Bus.

To achieve the above objectives, the present invention provides an intelligent massage bathing system applied for a massage bathing equipment, comprising: a plurality of attached devices, a massage bathing control unit, an operating panel unit and a master control device.

In a preferred embodiment, the attached devices are provided for directly actuating relatively to the massage bathing equipment, the attached devices including at least one first attached device and at least one second attached device.

In a preferred embodiment, the massage bathing control unit is configured for controlling an actuation of the at least one second attached device.

In a preferred embodiment, the operating panel unit includes a display screen and a input operation module for inputting an instruction on the display screen, the display screen is configured to selectively display an actuated state of one or a combination of the attached devices.

In a preferred embodiment, the master control device is configured to be directly electrically connected with the at least one first attached device, so that the master control device commands to directly control the at least one first attached device to actuate relatively to the massage bathing equipment according to an instruction from the operating panel unit.

In a preferred embodiment, the intelligent massage bathing system further comprises at least one slave control device directly electrically connected with the master control device, so that the master control device commands to directly control the actuation of the at least one first attached device and/or the at least one slave control device, and the display screen is configured to selectively display the actuated state of one or a combination of the at least one slave control device and the attached devices.

Compared with the prior art, the present invention simplifies the process of installation of various types of the additional devices and reduces the difficulty for adding of various types of the additional attached devices and the slave control devices through the master control device. When a user needs to add a new attached device, all the user has to do is only loading the appropriate drivers. Due to the configuration of the mast control device, a portion of the attached devices and/or slave control devices can be directly operated without through the SPA controller. Thus, the present invention not only can simplify the controlling process, but also is suitable for connecting the attached devices controlled by the traditional SPA controller.

DESCRIPTION OF THE DRAWINGS

FIG. 11-a is an architectural schematic view of the intelligent massage bathing system according to a third preferred embodiment of the present invention;

FIG. 11-*b* is an architectural schematic view of the intelligent massage bathing system according to a fourth preferred embodiment of the present invention;

FIG. 12-*a* is an architectural schematic view of the intelligent massage bathing system according to a fifth preferred embodiment of the present invention;

FIG. 12-*b* is an architectural schematic view of the intelligent massage bathing system according to a sixth preferred embodiment of the present invention;

FIG. 31 is a flowchart of a controlling method of the intelligent massage bathing system of the present invention.

DETAILED DESCRIPTION OF THE PREFERRED EMBODIMENTS

Figure 1:
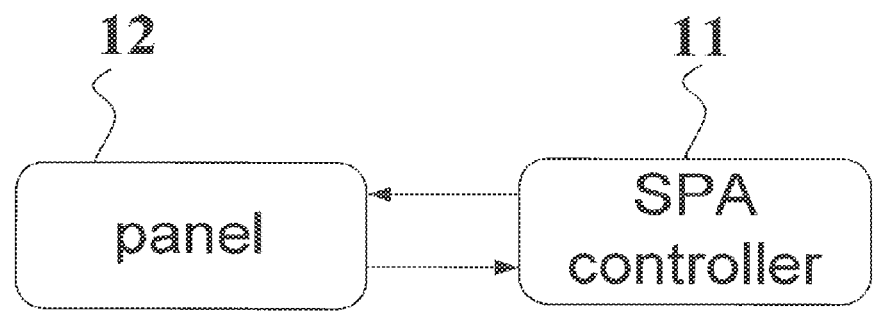
FIG. 1 is an architectural schematic view of the first conventional massage bathing system.
Figure 2:
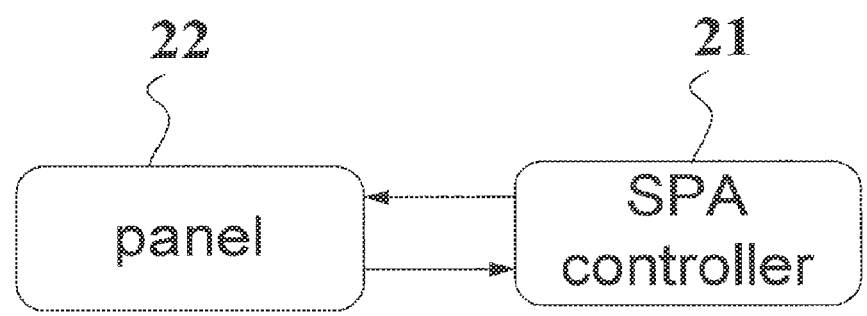
FIG. 2 is an architectural schematic view of the second conventional massage bathing system.
Figure 3:
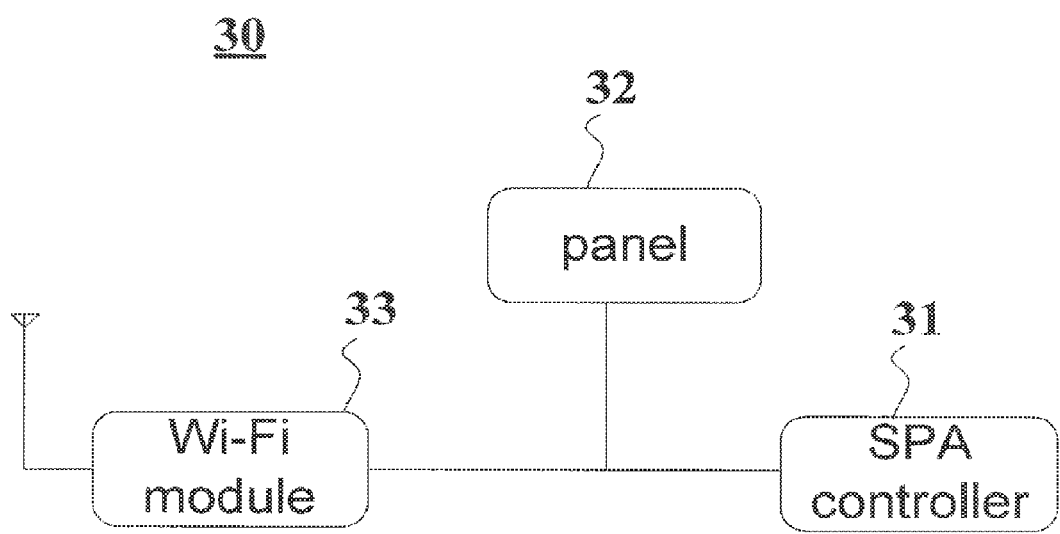
FIG. 3 is an architectural schematic view of the third conventional massage bathing system.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation, do not limit the scope of the invention.

Figure 4:
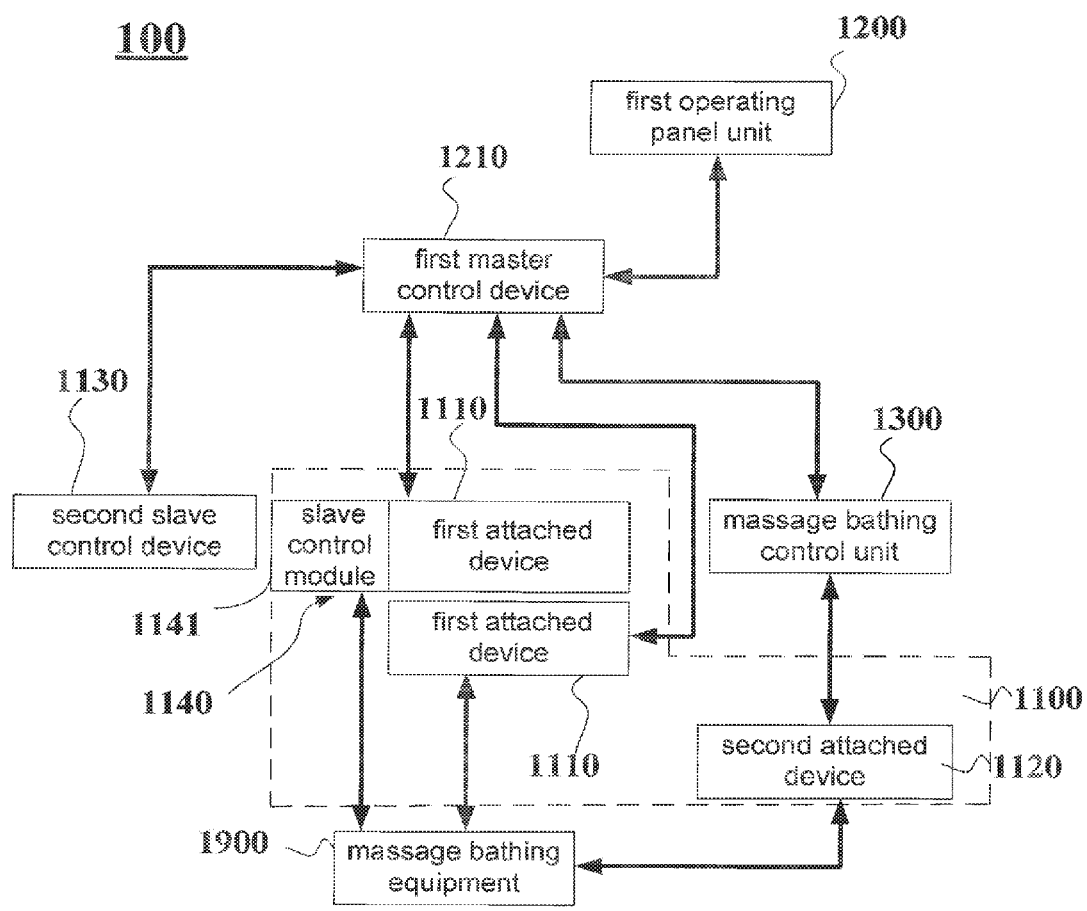
FIG. 4 is an architectural schematic view of an intelligent massage bathing system according to a first preferred embodiment of the present invention.

Now referring to FIG. 4, FIG. 4 is an architectural schematic view of an intelligent massage bathing system 100 according to a first preferred embodiment of the present invention. The intelligent massage bathing system 100 applied for a massage bathing equipment 1900 comprises a plurality of attached devices 1100, a first operating panel unit 1200, a first master control device 1210 and a massage bathing control unit 1300. The massage bathing equipment 1900 may include, but not limited to, a massage bathtub/hot tub, a SPA pool, a swimming pool or other equipment having the same or similar functions.

Referring to FIG. 4, the main function of the attached devices 1100 is provided for directly actuating relatively to the massage bathing equipment (to be described in detail below). The attached devices 1100 comprise at least one first attached device 1110 and at least one second attached device 1120. A portion of the at least one first attached device 1110 further comprises a slave control module 1141 such as a slave chip or a slave program, correspondingly to the first master control device 1210, for configuring the at least one first attached device 1110 as the at least one first slave control device 1140. The first master control device 1210 itself has a master control function with a plurality of drive control components and a multitasking kernel (referring to FIG. 7). The first master control device 1210 establishes a master-slave connection or a master-slave protocol with the at least one first slave control device 1140 through various communication protocols for directly controlling the at least one first slave control device 1140 and for expanding the other functions of the at least one first slave control device 1140 without controlling of the massage bathing control unit 1300. Based on the same principle, the intelligent massage bathing system 100 also can be additionally connected with the at least one second slave control device 1130 for expanding the other functions. The first master control device 1210 establishes the master-slave connection with the at least one second slave control device 1130 so that the first master control device 1210 commands to directly control the actuation of the at least one second slave control device 1130 without controlling through the massage bathing control unit 1300. Also, the first master control device 1210 can command to directly control the massage bathing control unit 1300 so as to fully support a conventional massage bathing equipment. However, in addition to a portion of the first attached devices 1110 configured as the at least one first slave control device 1140 as mentioned above, the other portion of the first attached devices 1110 (such as sensors) do not need adding the slave control module 1141 (such as a slave chip or a slave program) to configure as the first slave control device 1140. Namely, the attached devices 1110 can be directly controlled by the first master control device 1210.

The at least one first attached device 1110, the at least one first slave control device 1140, the at least one second slave control device 1130 and the at least one second attached device 1120 are interconnected through the communication protocols which comprise one or a combination of several of RS-485, RS-232, RS-422, I2C, USB, SPI, UART, CAN Bus and LIN Bus, for providing a capability to transmit information to the first master control device 1210 or receive information from the first master control device 1210. Besides, other electronic equipment (such as a microphone, not shown) can directly transmit information to the first master control device 1210 without adding the slave control module 1141.

Figure 6:
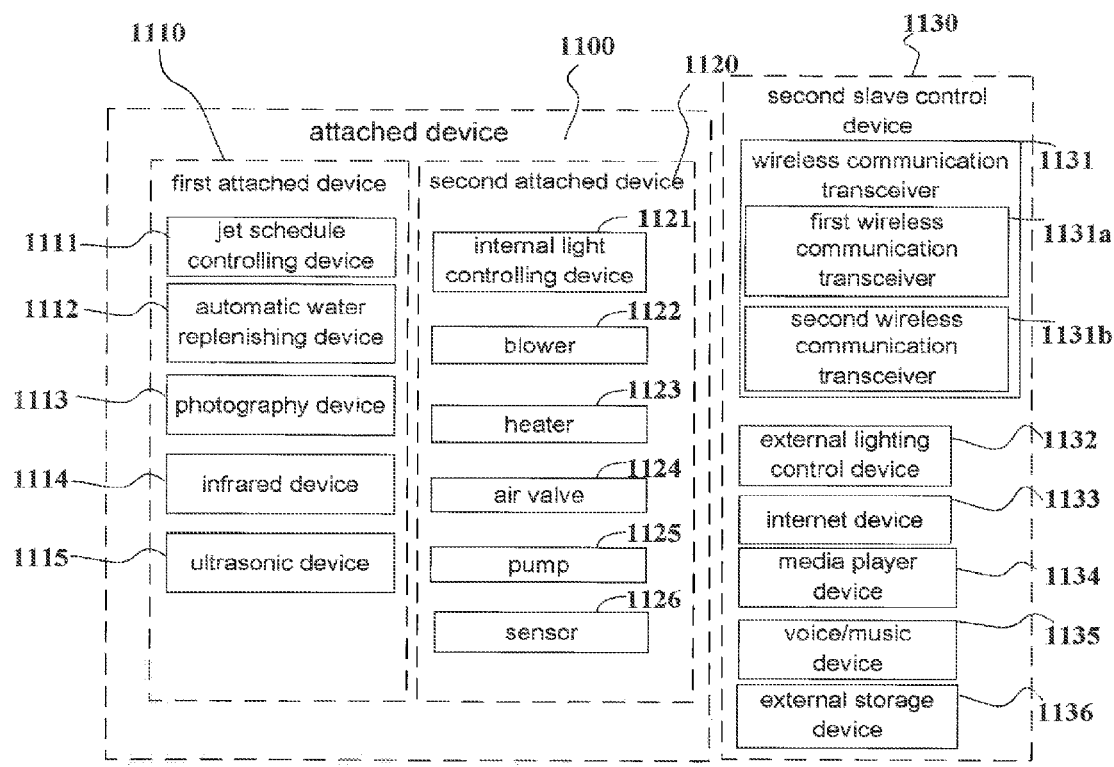
FIG. 6 is an architectural schematic view of the attached devices and the second slave control devices, according to FIG. 4.

Further referring to FIG. 4 and FIG. 6, the first attached device 1110 may include, but not limited to, one or a combination of several of a jet schedule controlling device 1111, an automatic water replenishing device 1112, an infrared device 1114, a photography device 1113 and an ultrasonic device 1115. In other embodiment of the present invention, the jet schedule controlling device 1111 and the automatic water replenishing device 1112 can be configured as the first slave control devices 1140. The at least one second attached device 1120 may include, but not limited to, one or a combination of several of a blower 1122, an air valve 1124, a sensor 1126, a pump 1125, an internal light controlling device 1121, a heater 1123 and a motor 1127 (referring to FIG. 8). The at least one second slave control device 1130 may include, but not limited to, one or a combination of several of at least one wireless communication transceiver 1131, an external lighting control device 1132, a media player device 1134, an internee device 1133, an external storage device 1136 and a voice/music device 1135. In this embodiment of the present invention, both or one of the massage bathing control unit 1300 and the first operating panel unit 1200 can be configured as one of the second slave control devices 1130.

Further referring to FIG. 4 and FIG. 6, the at least one wireless communication transceiver 1131 comprises one or both of at least one first wireless communication transceiver 1131a for a remote transfer and at least one second wireless communication transceiver 1131b for a proximal transfer. The at least one first wireless communication transceiver 1131a may include, but not limited to, a Wi-Fi transceiver. The at least one second wireless communication transceiver 1131b may include, but not limited to, one or a combination of several of a Zigbee transceiver, a RF transceiver and a Bluetooth transceiver. Moreover, the at least one first attached device 1110 further may include various types of analog/digital controllers or sensors, various types of physical or chemical sensors, etc. The second slave control device 1130 further may include biometric identification unit, image processing capturing unit, independent host device (with operating system (OS), library or application (APP)), voice processing/capturing unit, security/privacy protection/preservation surveillance systems, voice control unit, remote detection mechanism, various types of human-machine interfaces or user operation panel units, wearable device with multi-mode operation and so on.

Referring to FIG. 4 and FIG. 6, in this embodiment of the present invention, the internal light controlling device 1121 and the external lighting control device 1132 are used for controlling the internal ambient or atmosphere lighting of the massage bathing equipment 1900 and the external ambient or atmosphere lighting of the massage bathing equipment 1900, respectively.

Figure 5:
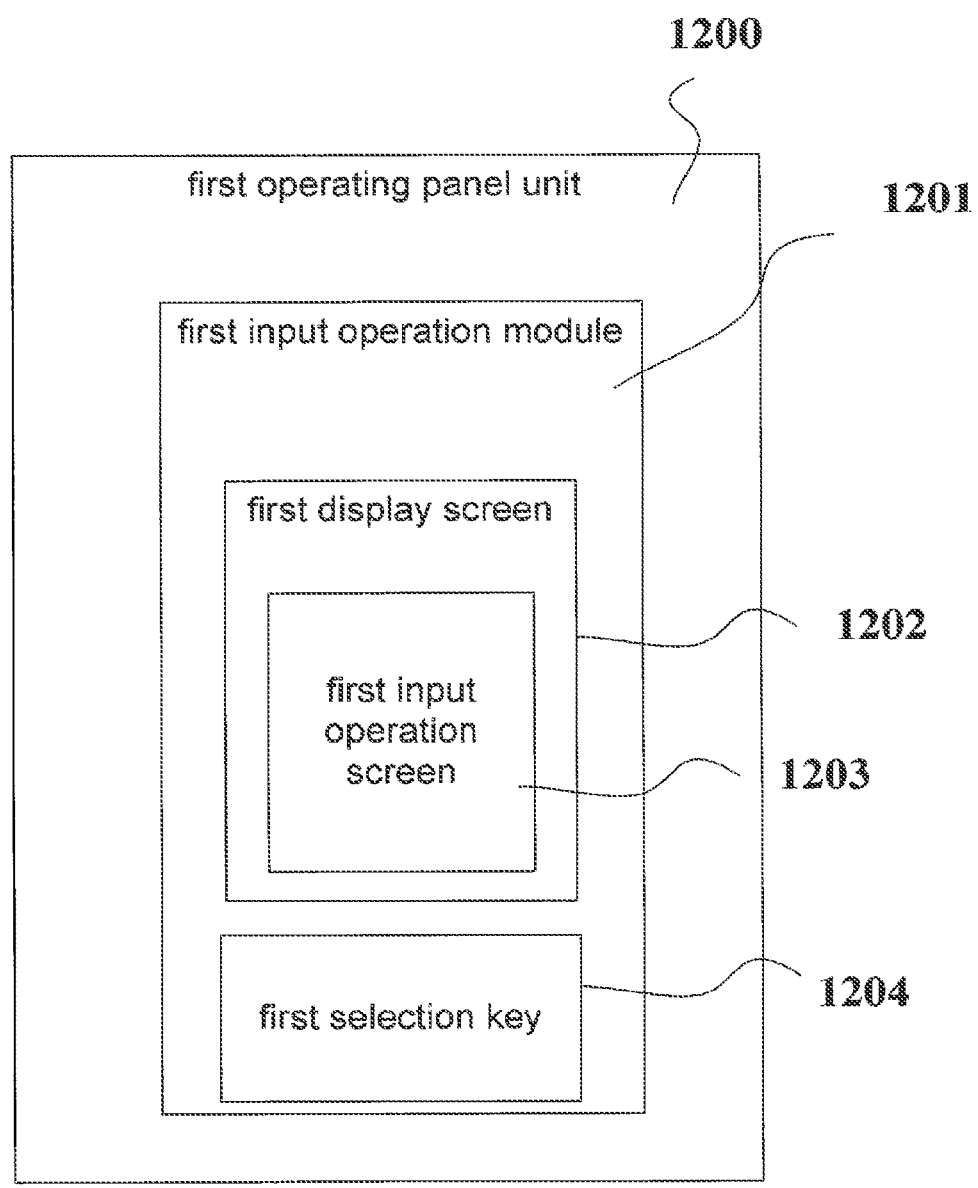
FIG. 5 is an architectural schematic view of the first operating panel unit according to FIG. 4.

Referring to FIG. 4 and FIG. 5, the first operating panel unit 1200 is a touch LCD panel or a non-touch LCD panel. The first operating panel unit 1200 includes a first display screen 1202 and a first input operation module 1201. The first input operation module 1201 comprises at least one first selection key 1204, a first input operation screen 1203, or combinations thereof for providing a user to input an instruction displayed on the first display screen 1202. The first display screen 1202 is configured to selectively display an actuated state of one or a combination of several of the at least one first slave control device 1140, the at least one second slave control device 1130, the other first attached devices 1110, the at least one second attached device 1120 and the other electronic products. The first input operation screen 1203 displays at least one functional icon, function menu or function input column on the first display screen for the user to click and generate the instruction. The instruction is used to correspondingly control one or a combination of several of actuations of the at least one first slave control device 1140, the at least one second slave control device 1130, the other first attached devices 1110, and the at least one second attached device 1120.

Figure 7:
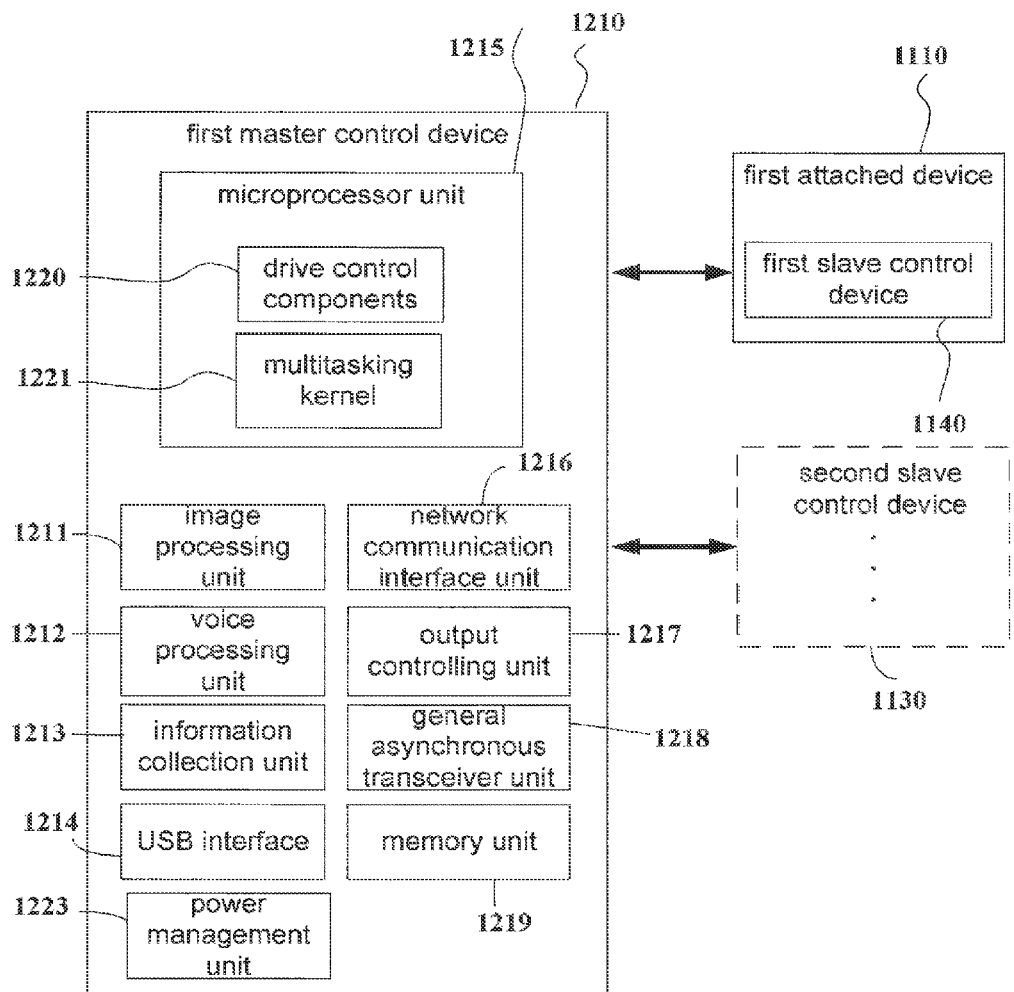
FIG. 7 is an architectural schematic view of the first master control device respectively establishing a master-slave connection with each of the first slave control device and the second slave control devices, according to FIG. 4.

Referring to FIG. 4 and FIG. 7, the first master control device 1210 can include, but not limited to, a memory unit 1219, a network communication interface unit 1216, a general asynchronous transceiver unit 1218, a microprocessor unit 1215, an image processing unit 1211, an voice processing unit 1212, an information collection unit 1213, an output controlling unit 1217, a USB interface 1214 and a power management unit 1223. The microprocessor unit 1215 comprises a plurality of drive control components 1220 and a multitasking kernel 1221. Essentially, the intelligent massage bathing system 100 according to the present invention is established on an Internet of Things (IOT) architecture. The first master control device 1210 is an embedded microprocessor architecture (such as ARM-based single-chip (SOC) or other similar multiple instruction set processor) with a built-in multitasking kernel (such as multi-threads). The first master control device 1210 not only connects to different slave control devices 1140, 1130 or any other slave device that needs to be expanded through a variety of built-in interfaces and/or libraries (PLL), but also uses the drive control components 1220 and the multitasking kernel 1221 of the microprocessor unit 1215 to establish the master-slave connection for directly controlling the first slave control device 1140 and the second slave control device 1130, respectively. The first master control device 1210 integrates and processes different types of signals/data stream from/to different slave control devices 1140, 1130 for expanding different functions. In this embodiment of the present invention, the drive control components 1220 can be a plurality of drivers, and the multitasking kernel 1221 can be multi-threads.

Figure 8:
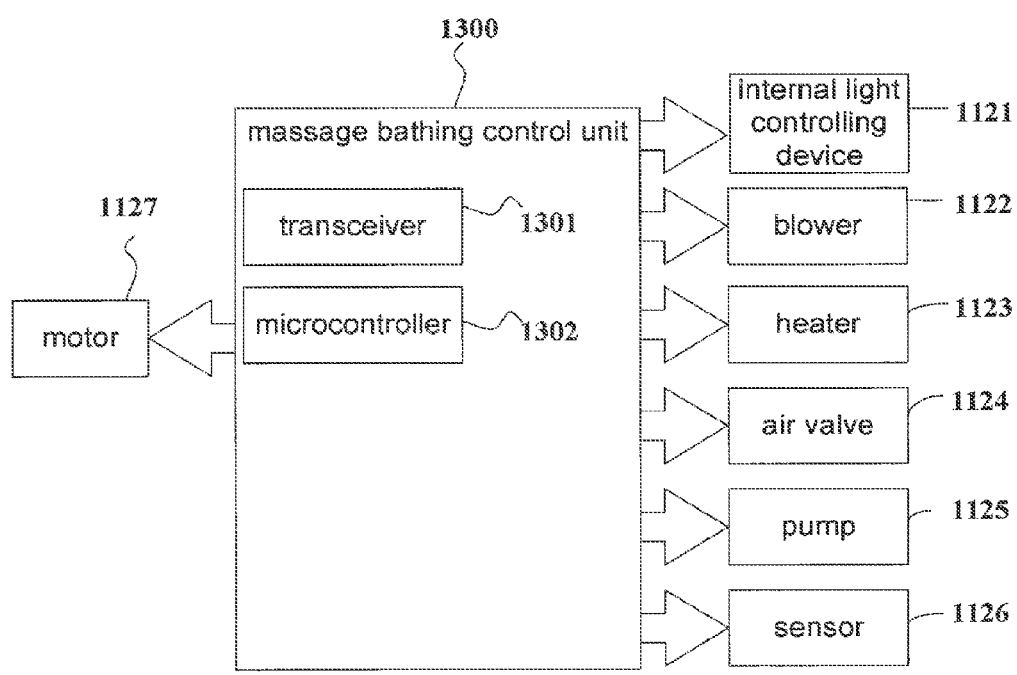
FIG. 8 is an architectural schematic view of the massage bathing control unit connecting with each second attached device according to FIG. 4.

Referring to FIG. 4 and FIG. 8, the massage bathing control unit 1300 comprises a transceiver 1301 and a microcontroller 1302. The microcontroller 1302 receives the instruction from the first master control device 1210, through the transceiver 1301, for controlling the at least one second attached device 1120. As shown in FIG. 8, the at least one second attached device 1120, such as a blower 1122, a motor 1127, an aft valve 1124, a sensor 1126, a pump 1125, an internal light controlling device 1121 and a heater 1123 and so on, is controlled by the massage bathing control unit 1300 for actuation.

Figure 9:
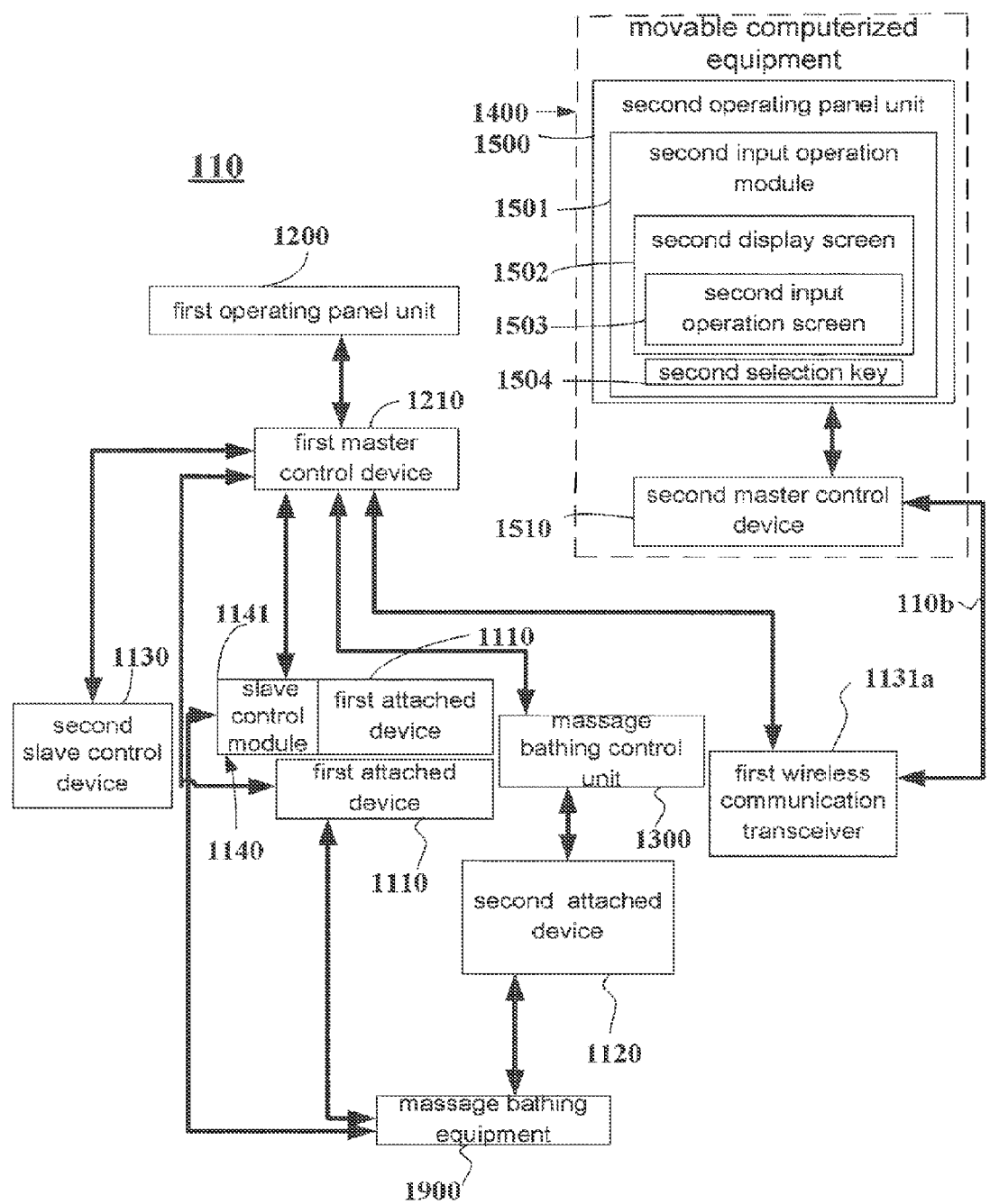
FIG. 9 is an architectural schematic view of the intelligent massage bathing system according to a second preferred embodiment of the present invention.

Referring to FIG. 9, FIG. 9 is an architectural schematic view of the intelligent massage bathing system 110 according to a second preferred embodiment of the present invention. The difference between the second preferred embodiment and the first preferred embodiment is that the intelligent massage bathing system 110 performs a networking connection to a remote movable computerized equipment 1400 through the first wireless communication transceiver 1131a. In the second preferred embodiment of the present invention, the second master control device 1510 of the remote movable computerized equipment 1400 can replace the first master control device 1210 and a second operating panel unit can replace the first operating panel unit 1200. Thus, when the user locates far away from the massage bathing equipment 1900, or any one of the first master control device 1210 and/or the first operating panel unit 1200 malfunction or get damaged, the user still can operate on the intelligent massage bathing system 110 to control one or several of actuations of the at least one first slave control device 1140, the at least one second slave control device 1130, the at least one second attached device 1120 and the other electronic devices through the movable computerized equipment 1400.

The intelligent massage bathing system 110 comprises a wireless communication network architecture 110b, a second operating panel unit 1500 and a second master control device 1510. The second operating panel unit 1500 includes a second display screen 1502 and a second input operation module 1501. The second input operation module 1501 comprises at least one second selection key 1504, a second input operation screen 1503, or combinations thereof, for providing a user to input an instruction on the second display screen 1502. Other functions of the second operating panel unit 1500 are the same as the first operating panel unit 1200 and will not repeat therein.

Figure 10:
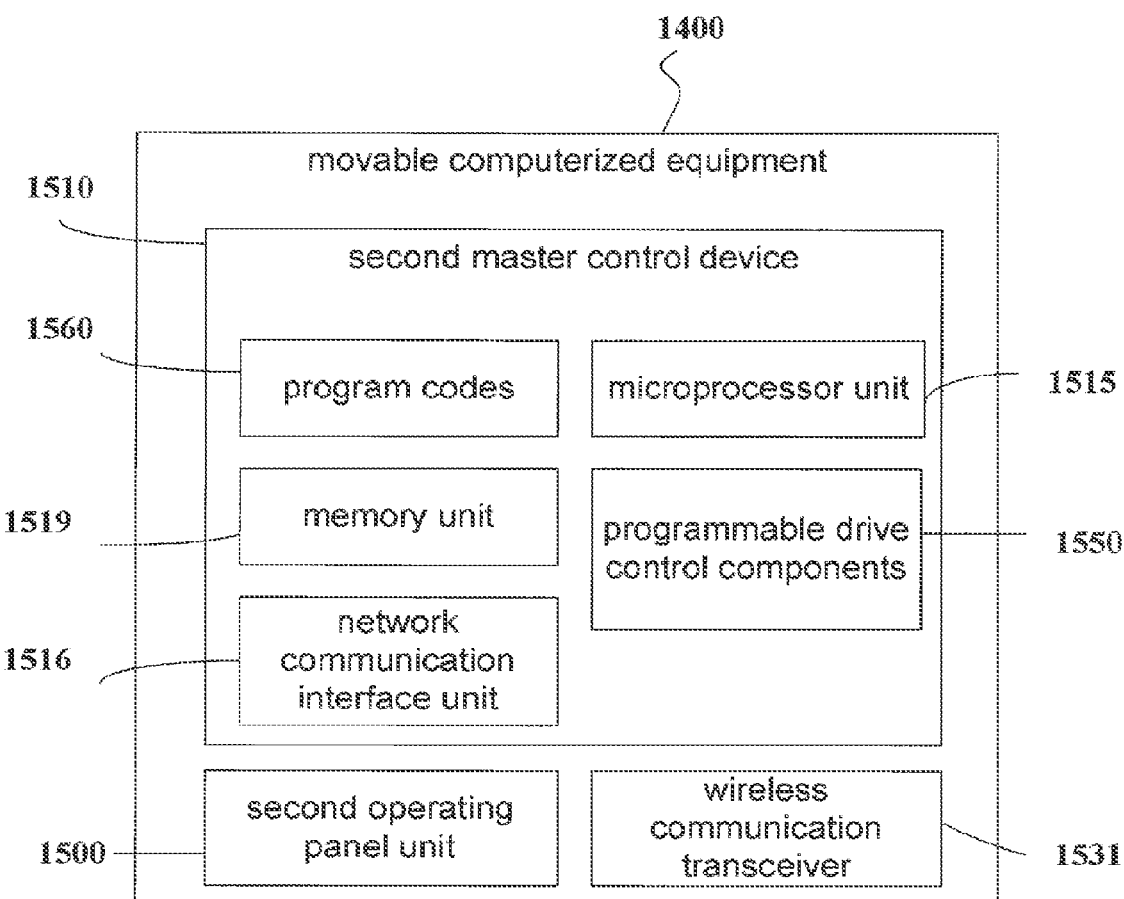
FIG. 10 is an architectural schematic view of the movable computerized equipment according to FIG. 9.

Referring to FIG. 9 and FIG. 10, FIG. 10 is an architectural schematic view of the movable computerized equipment according to FIG. 9. The second master control device 1510 of the movable computerized equipment 1400 includes, but not limited to, a memory unit 1519, a network communication interface unit 1516, a wireless communication transceiver 1531, a microprocessor unit 1515, a plurality of programmable drive control components 1550 and program codes 1560 for generating the second input operation screen (such as App or other operation interface programs). The microprocessor unit 1515 and the programmable drive control components 1550 are configured to process the master-slave connection for directly controlling the first slave control device 1140 and the second slave control device 1130. The movable computerized equipment 1400 can be a mobile phone, a tablet PC, a notebook or other communication equipments with communication protocols the same as the first wireless communication transceiver 1131a.

Referring to FIG. 11-a, FIG. 11-a is an architectural schematic view of the intelligent massage bathing system 120 according to a third preferred embodiment of the present invention. The difference between the third preferred embodiment and the second preferred embodiment is that: an intelligent massage bathing system 120 of the third preferred embodiment utilizes a data bus network architecture 110a to connect the first master control device 1210, the second slave control device 1130, the first slave control device 1140, the massage bathing control unit 1300 and the first wireless communication transceiver 1131a. In this embodiment of the present invention, it should be noted that the massage bathing control unit 1300 and the first wireless communication transceiver 1131a can be configured as the second slave control device 1130 which is directly controlled by the first master control device 1210 through the data bus network architecture 110a.

Referring to the third preferred embodiment of FIG. 11-a, the data bus network architecture 110a is an industrial bus architecture with concatenation function and multi-transmit properties, such as RS-485 architecture, but is not thereto In other embodiments, the data bus network architecture 110a also can be an industrial bus architecture with concatenation function, star connection function or cyclic connection function and multi-transmit properties, such as CAN Bus and LIN Bus. The data bus network architecture 110a comprises a first region master node and a plurality of first region slave nodes for electrically connecting with the first region master node, a portion of the at least one first slave control device 1140 and/or a portion of the second slave control devices 1130 are respectively disposed on the first region slave nodes, the first master control device is disposed on the first region master node. The massage bathing control unit 1300 configured as one of the second slave control device 1130 is disposed on one of the first region slave node. The first wireless communication transceiver 1131a (such as a Wi-Fi transceiver) belonging to the second slave control device 1130 is disposed on another first region slave node. Apart from the at least one second attached device 1120, each of the at least one first slave control device 1140 and/or the second slave control device 1130 can be directly controlled by the first master control device 1210 base on the master-slave connection through the data bus network architecture 110a. Due to the characteristics of the RS-485, a slave-slave connection is established for transmitting the messages and/or for directly controlling among the first slave control device 1140, the second slave control device 1130, the massage bathing control unit 1300 and the first wireless communication transceiver 1131a. In practice, the following examples may be established variety of the slave-slave connections.

EXAMPLE 1 a slave-slave connection is used for transmitting the signals. When the first master control device 1210 assigns a default task scheduler to each of the slave control device (such as the first slave control device 1140, the second slave control device 1130 and the massage bathing control unit 1300) through the data bus network architecture, each of the slave control device operates according to the request of the default task scheduler and transmits the signals to the other related slave control devices through the data bus network architecture 110a for transmitting the signals via the slave-slave connection. For example, after the jet schedule controlling device 1111 (shown in FIG. 6) of the first slave control device 1140 turning on its control valve according to the request of the default task scheduler, the jet schedule controlling device 1111 will transmit a notification signal to the massage bathing control unit 1300 through the data bus network architecture 110a. The massage bathing control unit 1300 also controls the pump 1125 (shown in FIG. 8), according to the notification signal, processing the request of the default task scheduler, for implementing the actuation of the jet schedule controlling device 1111. It should be noted that, based on the same operation principle, the movable computerized equipment 1400 also can assigns a default task scheduler to the first wireless communication transceiver 1131a of the second slave control device 1130 through the wireless communication network architecture 110b and then the default task scheduler is transferred to each of the slave control device through the data bus network architecture 110a for implementing the directly controlling mentioned above.

EXAMPLE 2 a slave-slave connection is used for controlling. When the first master control device 1210 assigns a default task scheduler to each of the slave control device (such as the massage bathing control unit 1300), the massage bathing control unit 1300 transmits a control signal to the other related slave control devices according to the request of the default task scheduler for establishing the slave-slave connection. For example, the massage bathing control unit 1300 belonging to the second slave control device 1130 transmit a control signal to the jet schedule controlling device 1111 (shown in FIG. 6) of the first slave control device 1140 for turning on its control valve according to the request of the default task scheduler through the data bus network architecture 110a. Then, the massage bathing control unit 1300 further controls the pump 1125 (shown in FIG. 8), according to the request of the default task scheduler, for implementing the actuation of the jet schedule controlling device 1111. It should be noted that, based on the same operation principle, the movable computerized equipment 1400 also can assigns a default task scheduler to the first wireless communication transceiver 1131a of the second slave control device 1130 through the wireless communication network architecture 110b and then the default task scheduler is transferred to each of the slave control device (including the massage bathing control unit 1300) through the data bus network architecture 110a. The massage bathing control unit 1300 will transmit a control signal to the other related slave control devices according to the default task scheduler for performing the controlling of the slave-slave connection.

EXAMPLE 3 a slave-slave, connection is used for controlling. When the movable computerized equipment 1400 assigns a control signal to one of the slave control devices (such as the first wireless communication transceiver 1131a which belongs to the second slave control device 1130) through the wireless communication network architecture 110b, and then one of the slave control devices transmits a control signal to the other related slave control devices (such as one of the second slave control device 1130, the first slave control device 1140 and the massage bathing control unit 1300, or any combination thereof), through the data bus network architecture 110a, for performing a slave-slave connection controlling. However, the first slave control device 1140 only comprises the first attached device 1110 but excludes the other specific devices such as a sensor. If the first slave control device 1140 comprises the first attached device 1110 such as a sensor, the first slave control device 1140 needs to pass through the first master control device 1210 for performing the master-slave connection controlling.

Referring to FIG. 11-b, FIG. 11-b is an architectural schematic view of the intelligent massage bathing system 130 according to a fourth preferred embodiment of the present invention. The difference between the fourth preferred embodiment and the third preferred embodiment is that the first master control device 1210 and the first operating panel unit 1200 are removed therefrom. In this embodiment of the present invention, the second master control device 1510 and the second operating panel unit 1500 of the movable computerized equipment 1400 and can completely replace the first master control device 1210 and the first operating panel unit 1200 shown in FIG. 11-a. Thus, even if the user locates in a remote place, or the first master control device 1210 and/or the first operating panel unit 1200 is lost, malfunctions or damaged, the user still can operate in the intelligent massage bathing system 130 through the movable computerized equipment 1400.

Referring to FIG. 12-a, FIG. 12-a is an architectural schematic view of the intelligent massage bathing system 140 according to a fifth preferred embodiment of the present invention. The difference between the fifth preferred embodiment and the second preferred embodiment is that a cloud server 1610 is added therein. Under the circumstances, the intelligent massage bathing system 140 performs a cloud mode since the intelligent massage bathing system 140 is connected with the cloud server 1610. The cloud server 1610 includes at least one cloud database for storing required information. In this embodiment of the present invention, the first wireless communication transceiver 1131a is a Wi-Fi transceiver for providing remote network connection. Namely, the wireless communication network architecture 110b can be connected to the internet. It indicates that the first master control device 1210 is connected to the cloud server 1610 through the first wireless communication transceiver 1131a and the wireless communication network architecture 110b for obtaining the information such as program updates or customer data. Alternatively, the second master control device 1510 of the movable computerized equipment 1400 is directly connected to the cloud server 1610 through the wireless communication network architecture 110b, and the cloud server 1610 is provided for downloading the programmable drive control components 1550 and for downloading the program codes of the second input operation screen generated by the second operating panel unit 1500. Furthermore, the movable computerized equipment 1400 can control one or several of actuations generated by the at least one first slave control device 1140, the other second slave control devices 1130 and the at least one second attached device 1120 controlled through the massage bathing control unit 1300, via the wireless communication network architecture 110b, the wireless communication transceiver 1131 and the first master control device 1210 sequentially.

Referring to FIG. 12-b, FIG. 12-b is an architectural schematic view of the intelligent massage bathing system 150 according to a sixth preferred embodiment of the present invention. The difference between the sixth preferred embodiment and the fifth preferred embodiment is in adding at least one second wireless communication transceiver 1131b in the sixth preferred embodiment (such as a Zigbee transceiver, a RF transceiver, a Bluetooth transceiver and any combination thereof, but is not limited thereto) and removing the first wireless communication transceiver 1131a. In this embodiment of the present invention, each of the at least one second slave control devices 1130' comprises one second wireless communication transceiver 1131b. Thus, the first master control device 1210 wireless controls the at least one second slave control device 1130' through the second wireless communication transceiver 1131b. In other embodiment of the present invention, the second wireless communication transceiver 1131b can be disposed within the at least one first slave control device 1140, and then the first master control device 1210 wireless controls the at least one first slave control device.

Figure 13:
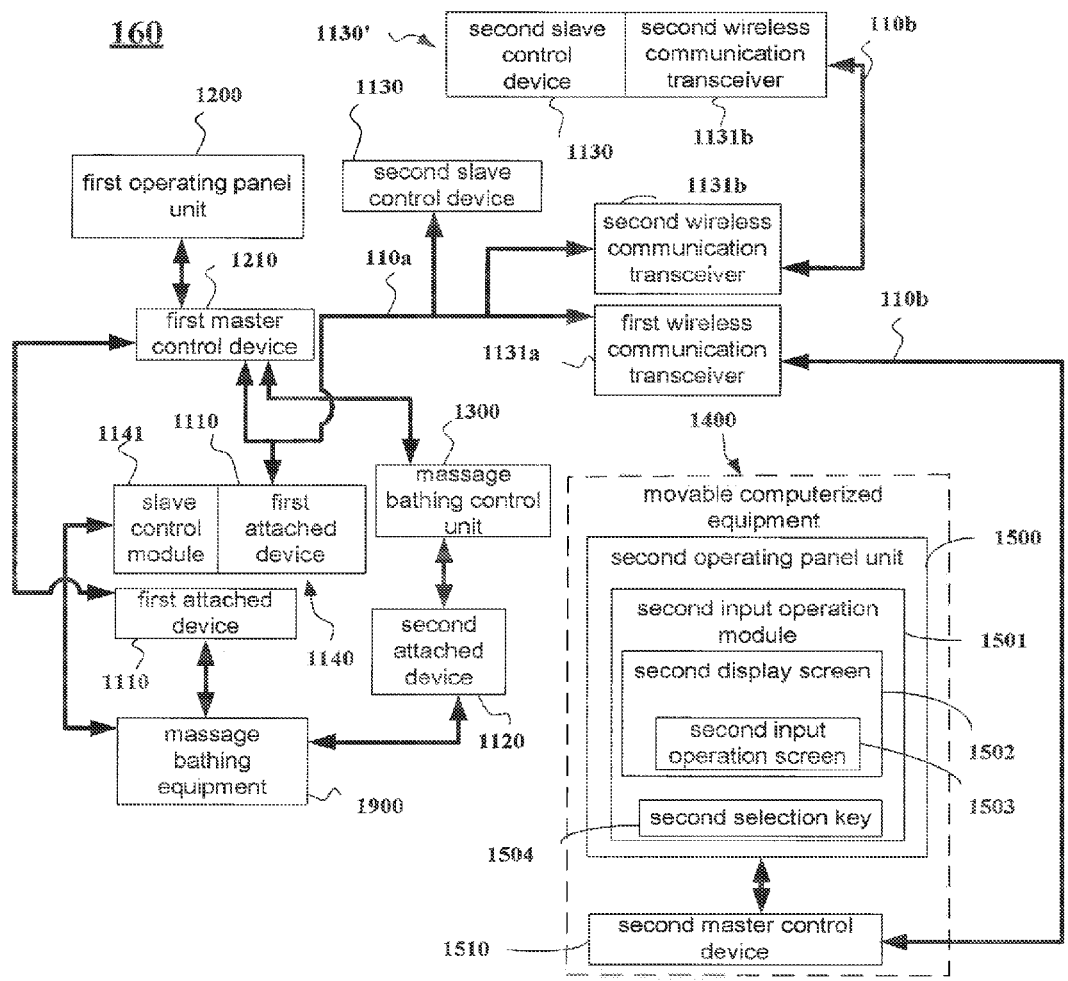
FIG. 13 is an architectural schematic view of the intelligent massage bathing system according to a seventh preferred embodiment of the present invention.

Referring to FIG. 13, FIG. 13 is an architectural schematic view of the intelligent massage bathing system 160 according to a seventh preferred embodiment of the present invention. The difference between the third preferred embodiment shown in FIG. 11-a and the seventh preferred embodiment are that: (1) a second wireless communication transceiver 1131b is added in the seventh preferred embodiment; (2) the massage bathing control unit 1300 of the seventh preferred embodiment is not connected to the data bus network architecture 110a (such as the RS-485) but connected to the first master control device 1210 directly through other communication interface; and (3) at least one second slave control device 1130' with the second wireless communication transceiver 1131b disposed therein is added in the seventh preferred embodiment. The data bus network architecture 110a (such as the RS-485) comprises a plurality of first region nodes for being disposed with the first master control device 1210, the first wireless communication transceiver 1131a, the second wireless communication transceiver 1131b and the first slave control device 1140. The first master control device 1210 is disposed on the first region master node, a part of the at least one second slave control device 1130 connected to first master control device 1210 through the data bus network architecture 110a. The controlling method is in accordance to a wired manner. The other part of each of the at least one second slave control device 1130' is controlled in a wireless manner via the second wireless communication transceiver 1131b disposed therein. Accordingly, the at least one second slave control device 1130', the first wireless communication transceiver 1131a, the second wireless communication transceiver 1131b, the at least one second slave control device 1130 and the first slave control device 1140 can be connected with each other to constitute an Internet of Things (IOT) architecture in a wired or wireless manner through the slave-slave connection, such as a p2p mode.

Figure 14:
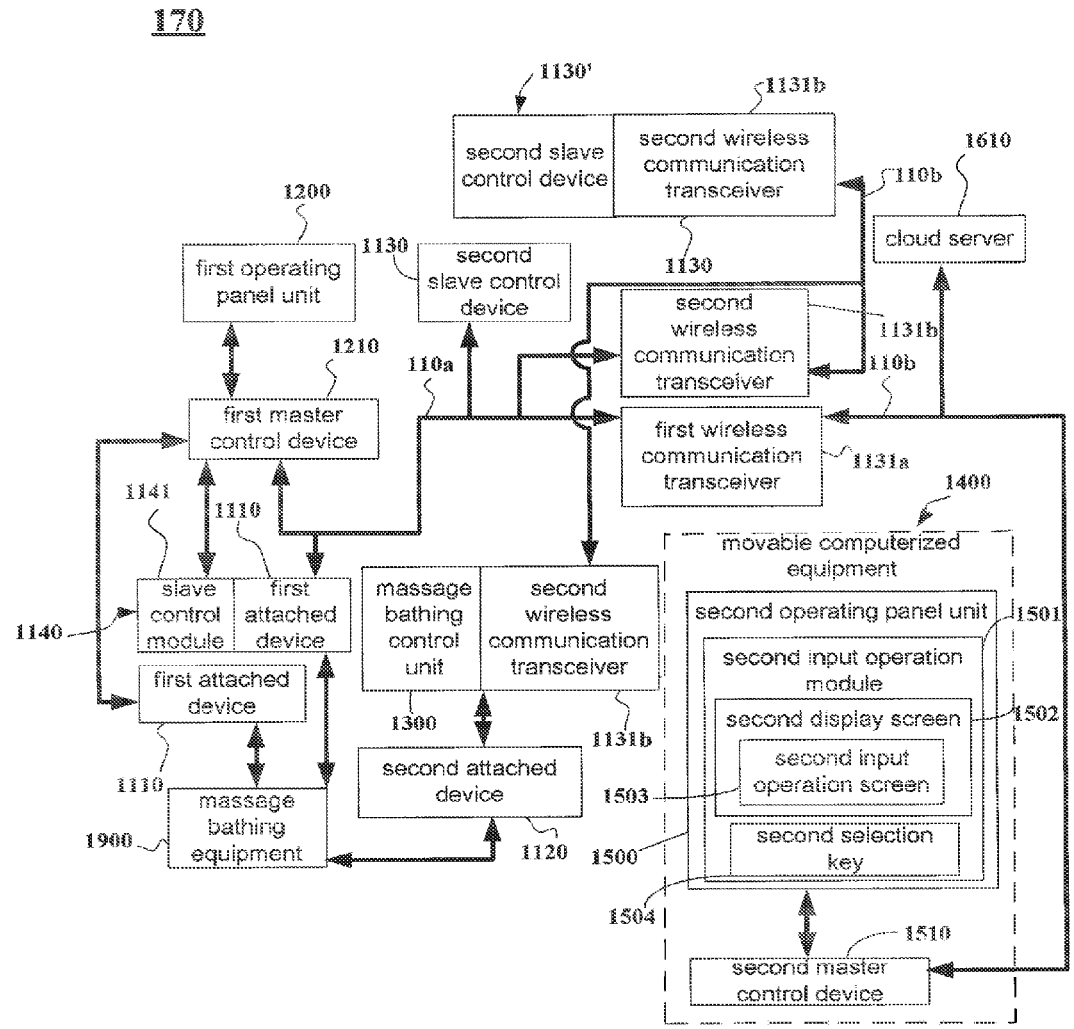
FIG. 14 is an architectural schematic view of the intelligent massage bathing system according to an eighth preferred embodiment of the present invention.

Referring to FIG. 14, FIG. 14 is an architectural schematic view of the intelligent massage bathing system 170 according to an eighth preferred embodiment of the present invention. The difference between the eighth preferred embodiment and the seventh preferred embodiment is in adding a cloud server 1610. The cloud server 1610 is connected to a plurality of the first slave control devices 1140, a plurality of the second slave control devices 1130, 1130', the first wireless communication transceiver 1131a and each of the second wireless communication transceiver 1131b, through the wireless communication network architecture 110b, so that each slave-slave connection is processed among different devices based on the Internet of Things (IOT) architecture. The massage bathing control unit 1300 additionally comprises the second wireless communication transceiver 1131b for connecting with the wireless communication network architecture 110b.

Figure 15:
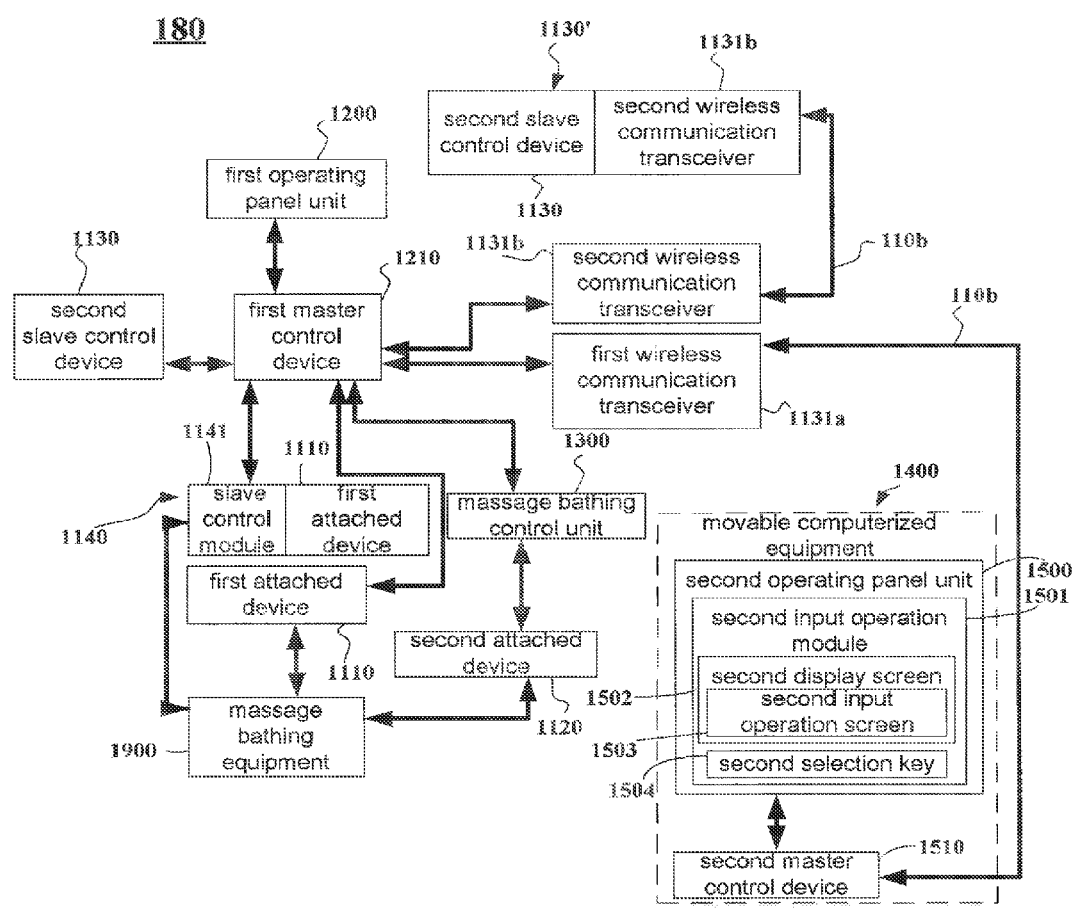
FIG. 15 is an architectural schematic view of the intelligent massage bathing system according to a ninth preferred embodiment of the present invention.

Referring to FIG. 15, FIG. 15 is an architectural schematic view of the intelligent massage bathing system 180 according to a ninth preferred embodiment of the present invention. The difference between the ninth preferred embodiment and the eighth preferred embodiment is that: the first wireless communication transceiver 1131a, the second wireless communication transceiver 1131b and the first slave control device 1140 of the ninth preferred embodiment are individually connected to the first master control device 1210 through different data bus interfaces. A portion of the at least one second slave control device 1130 are also respectively connected to the first master control device 1210 through the different data bus interfaces. The different data bus interfaces may be one or a combination of several of RS-485, CAN Bus, LIN Bus, RS-232, RS-422, I2C, SPI, USB and UART but not limited thereto. The other portion of the at least one second slave control device 1130' can be individually controlled in a wireless manner provided by the second wireless communication transceiver 1131b disposed therein.

Figure 16:
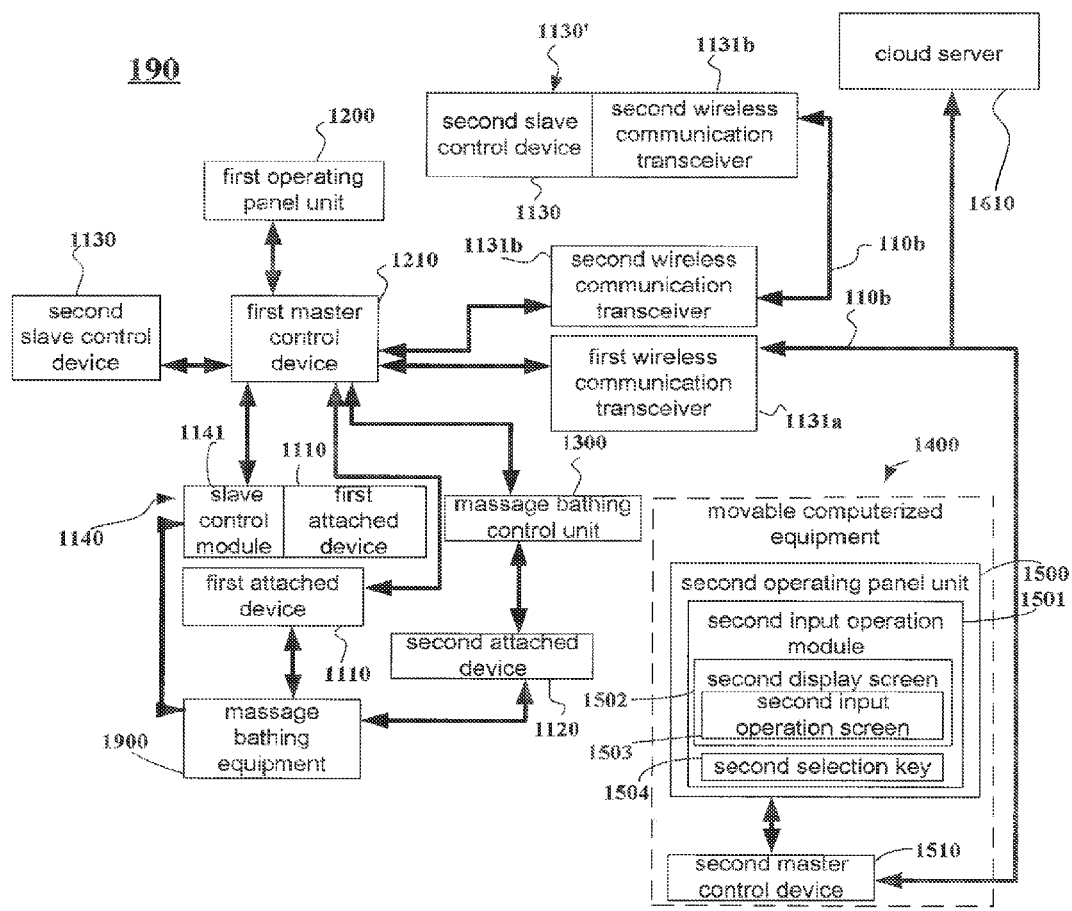
FIG. 16 is an architectural schematic view of the intelligent massage bathing system according to a tenth preferred embodiment of the present invention.

Referring to FIG. 16, FIG. 16 is an architectural schematic view of the intelligent massage bathing system 190 according to a tenth preferred embodiment of the present invention. The difference between the tenth preferred embodiment and the ninth preferred embodiment is in adding a cloud server 1610. The cloud server 1610 can be connected to a plurality of the second slave control devices 1130', the first wireless communication transceiver 1131a and the second wireless communication transceiver 1131b through the wireless communication network architecture 110b.

The following preferred embodiments will be introduced respectively, in which one of the massage bathing control unit 1300, the first operating panel unit 1200, the second slave control device 1130 and the at least one first attached device 1110 is integrally assembled with the first master control device 1210.

Figure 17:
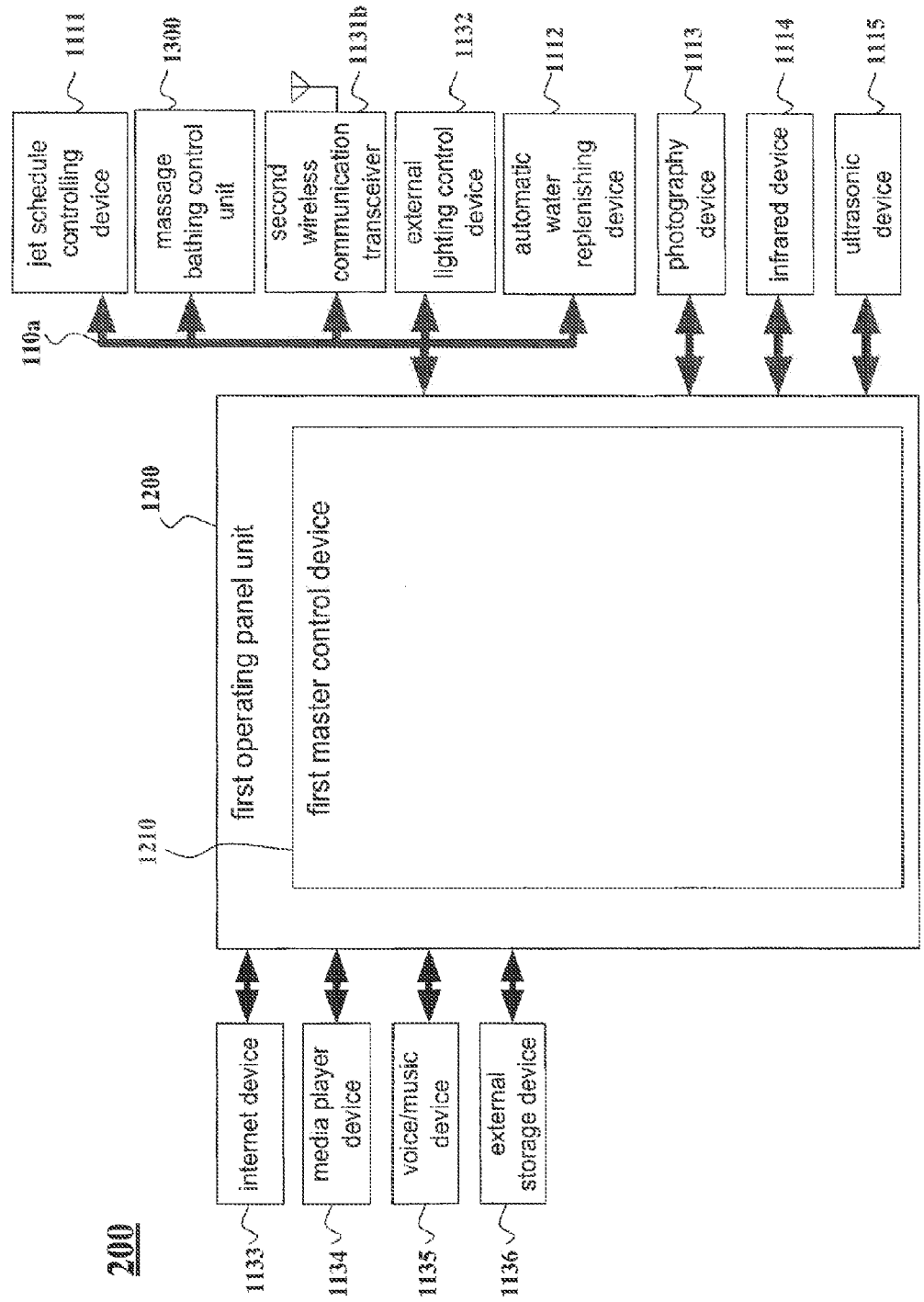
FIG. 17 is an architectural schematic view of the intelligent massage bathing system according to an eleventh preferred embodiment of the present invention.

Referring to FIG. 17, FIG. 17 is an architectural schematic view of the intelligent massage bathing system 200 according to an eleventh preferred embodiment of the present invention. The difference between the eleventh preferred embodiment and the first preferred embodiment is that: the first operating panel unit 1200 is integrally assembled with the first master control device 1210, and the first master control device 1210 comprises the second wireless communication transceiver 1131b. In this embodiment of the present invention, the first attached device 1110 comprises one or a combination of several of a jet schedule controlling device 1111, an automatic water replenishing device 1112, an infrared device 1114 and a ultrasonic device 1115. The second slave control devices comprises the massage bathing control unit 1300, the second wireless communication transceiver 1131b, an external lighting control device 1132, a photographic device 1113, an internet device 1133, a media player device 1134, a voice/music device 1135 and an external storage device 1136. As shown in FIG. 17, the jet schedule controlling device 1111, the massage bathing control unit 1300, the second wireless communication transceiver 1131b, the external lighting control device 1132 and the automatic water replenishing device 1112 shown in the upper right corner of FIG. 17 can be directly controlled via the data bus network architecture 110a, without control of the first master control device 1210. However, the photographic device 1113, the infrared device 1114, the ultrasonic device 1115 shown in the lower right corner of FIG. 17, the internet device 1133, the media player device 1134, the voice/music device 1135 and the external storage device 1136 shown in upper left corner of FIG. 17 must be controlled through the first master control device 1210. As mentioned above, the first master control device 1210 commands to directly control the first slave control device 1140 and the second slave control device 1130, via the master-slave connection, without control through the massage bathing control unit 1300.

Figure 18:
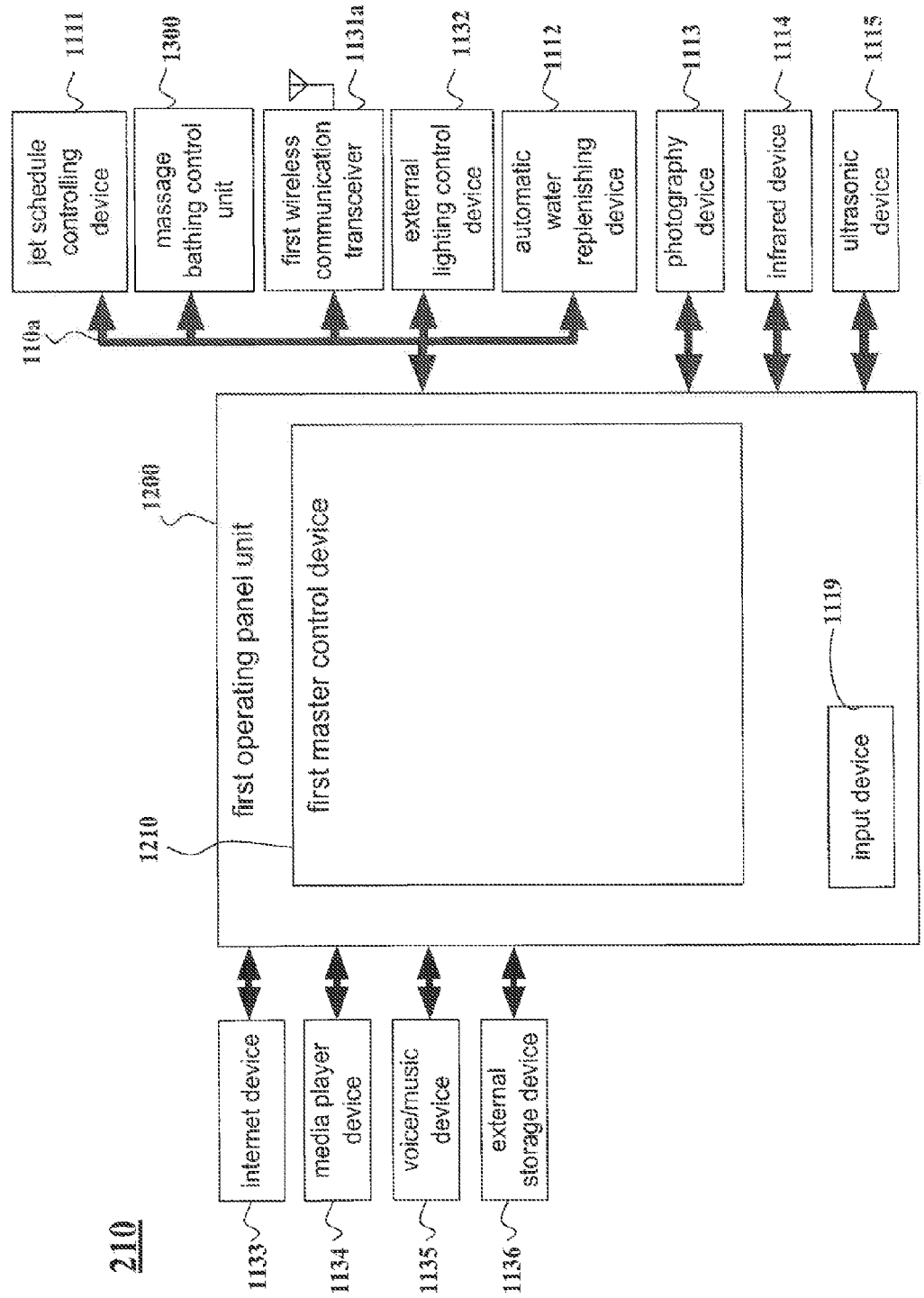
FIG. 18 is an architectural schematic view of the intelligent massage bathing system according to a twelfth preferred embodiment of the present invention.

Referring to FIG. 18, FIG. 18 is an architectural schematic view of the intelligent massage bathing system 210 according to a twelfth preferred embodiment of the present invention. The difference between the twelfth preferred embodiment and the eleventh preferred embodiment is that: the first operating panel unit 1200 further is connected to an input device 1119. The input device 1119 is a mouse, a keyboard or any device with the same communication protocol as the first master control device 1210.

Figure 19:
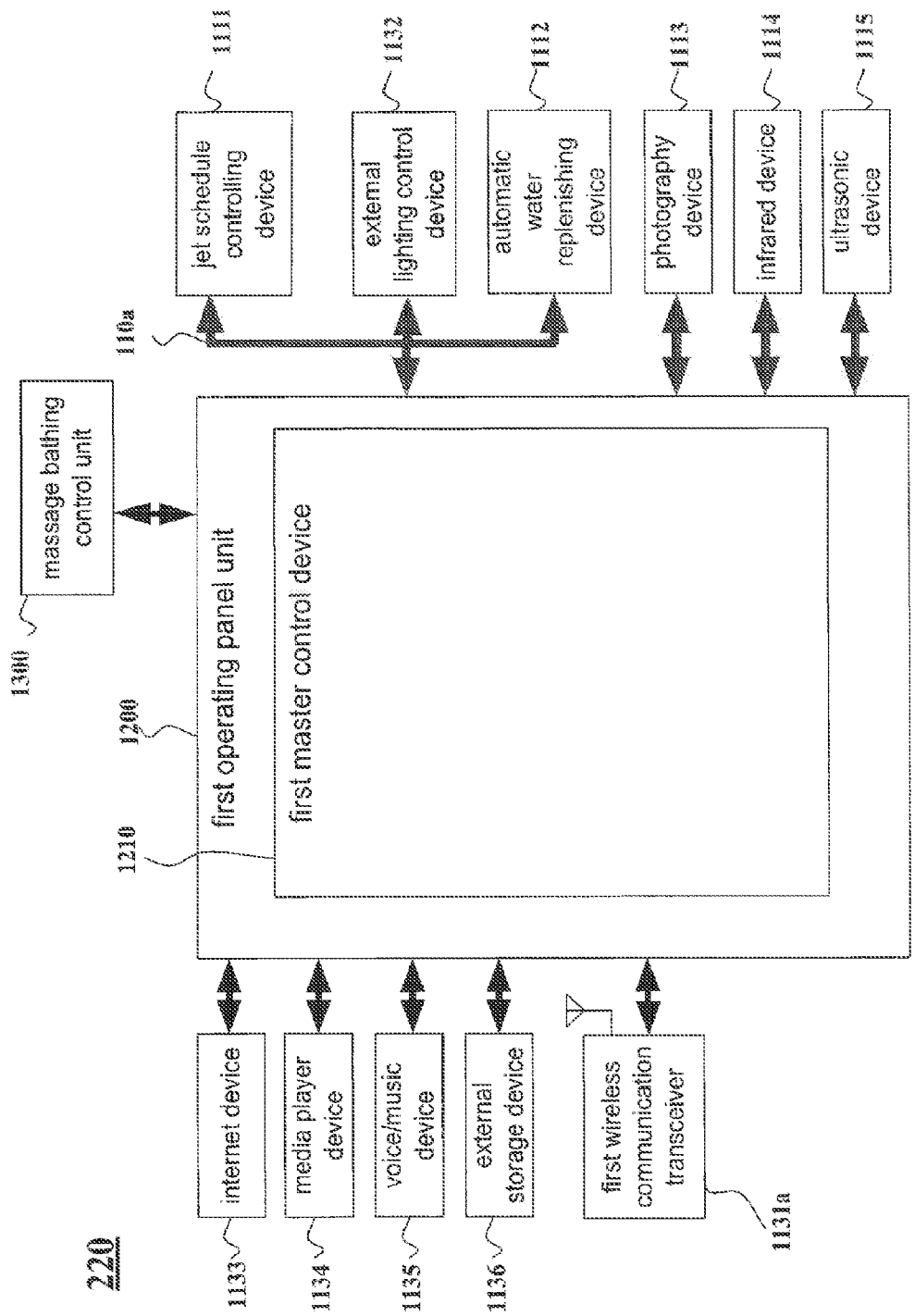
FIG. 19 is an architectural schematic view of the intelligent massage bathing system according to a thirteenth preferred embodiment of the present invention.

Referring to FIG. 19, FIG. 19 is an architectural schematic view of the intelligent massage bathing system 220 according to a thirteenth preferred embodiment of the present invention. The difference between the thirteenth preferred embodiment and the twelfth preferred embodiment is that: the first wireless communication transceiver 1131*a* and the massage bathing control unit 1300 are not disposed within the data bus network architecture 110*a*. The first wireless communication transceiver 1131*a* and the massage bathing control unit 1300 are connected to the first master control device 1210 via other communication interfaces, directly. In other words, when an instruction is sent by the second master control device 1510 and received by the wireless communication transceiver 1131, all the instructions must pass through the first master control device 1210 for further transmitting to any one of the first slave control device 1140, the other second slave control devices 1130, and the attached device 1120 which is controlled by the massage bathing control unit 1300.

Figure 20:
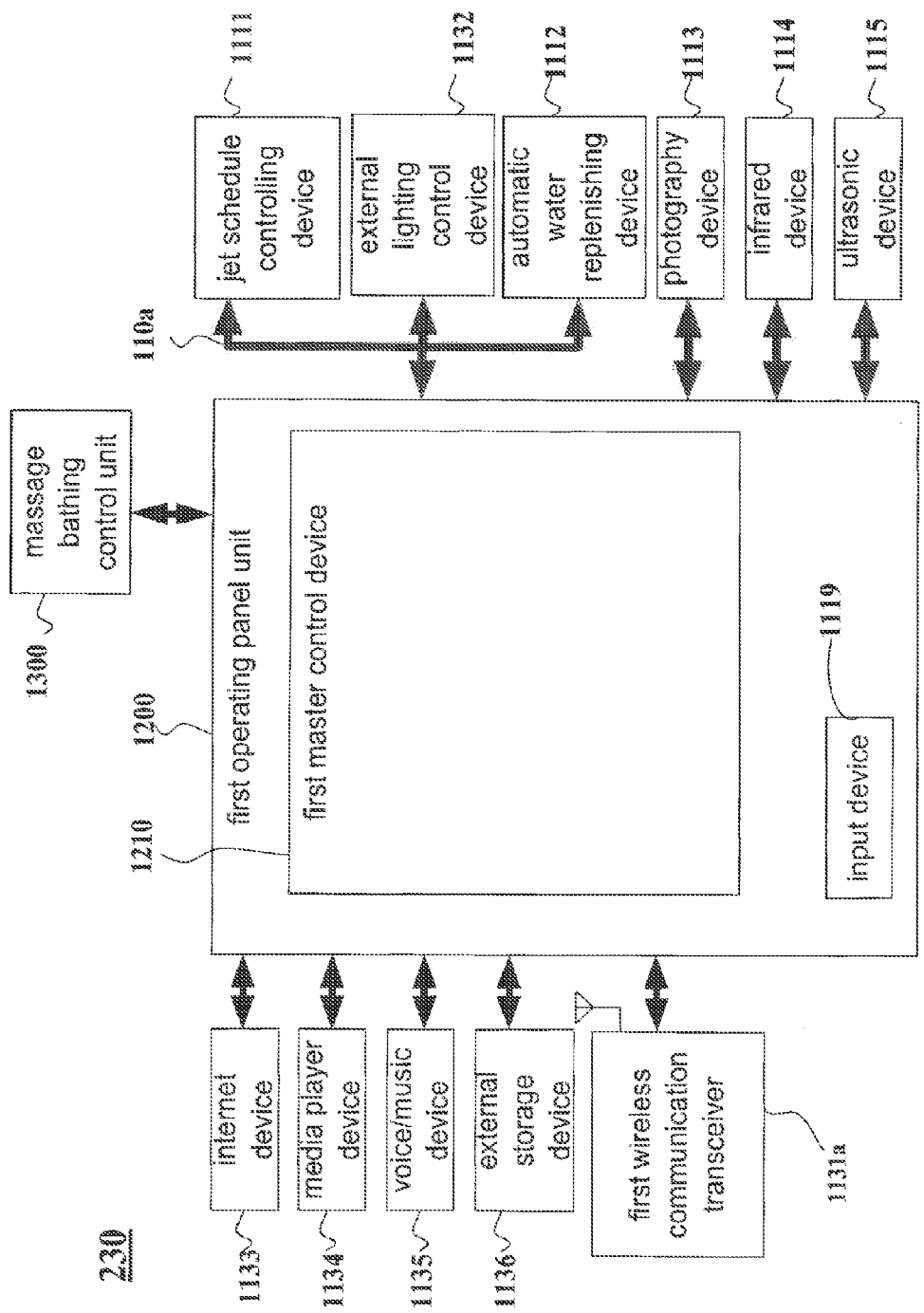
FIG. 20 is an architectural schematic view of the intelligent massage bathing system according to a fourteenth preferred embodiment of the present invention.

Referring to FIG. 20, FIG. 20 is an architectural schematic vie of the intelligent massage bathing system 230 according to a fourteenth preferred embodiment of the present invention. The difference between the fourteenth preferred embodiment and the thirteenth preferred embodiment is that: the first operating panel unit 1200 is further connected to an input device 1119. The input device 1119 is a mouse, a keyboard or any device with the same communication protocol as the first master control device 1210.

Figure 21:
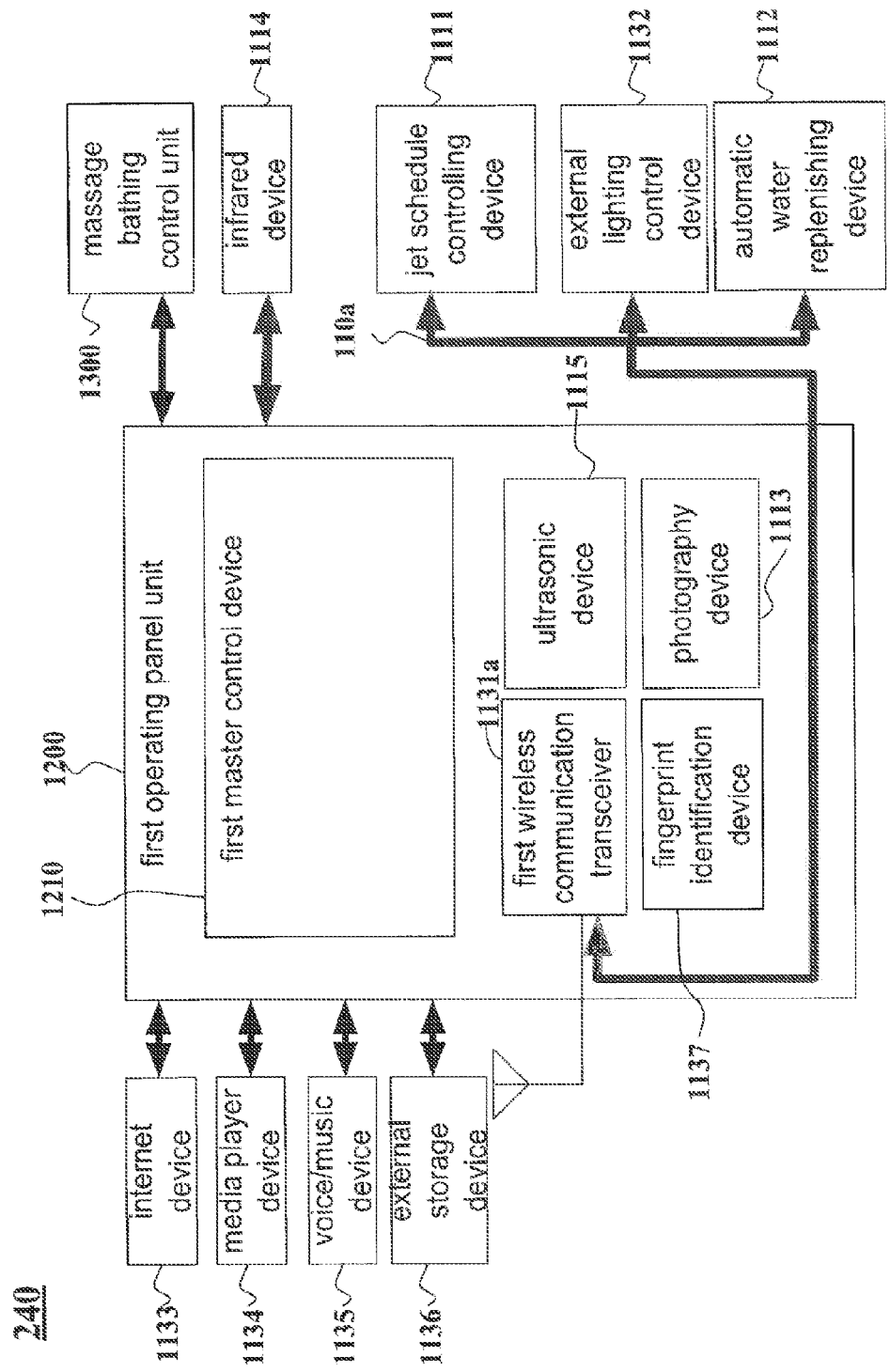
FIG. 21 is an architectural schematic view of the intelligent massage bathing system according to a fifteenth preferred embodiment of the present invention.

Referring to FIG. 21, FIG. 21 is an architectural schematic view of the intelligent massage bathing system 240 according to a fifteenth preferred embodiment of the present invention. The difference between the fifteenth preferred embodiment and the thirteenth preferred embodiment is that: the first wireless communication transceiver 1131*a*, the photography device 1113, the ultrasonic device 1115 and a fingerprint identification device 1137 are integrally assembled with the first operating panel unit 1200.

Figure 22:
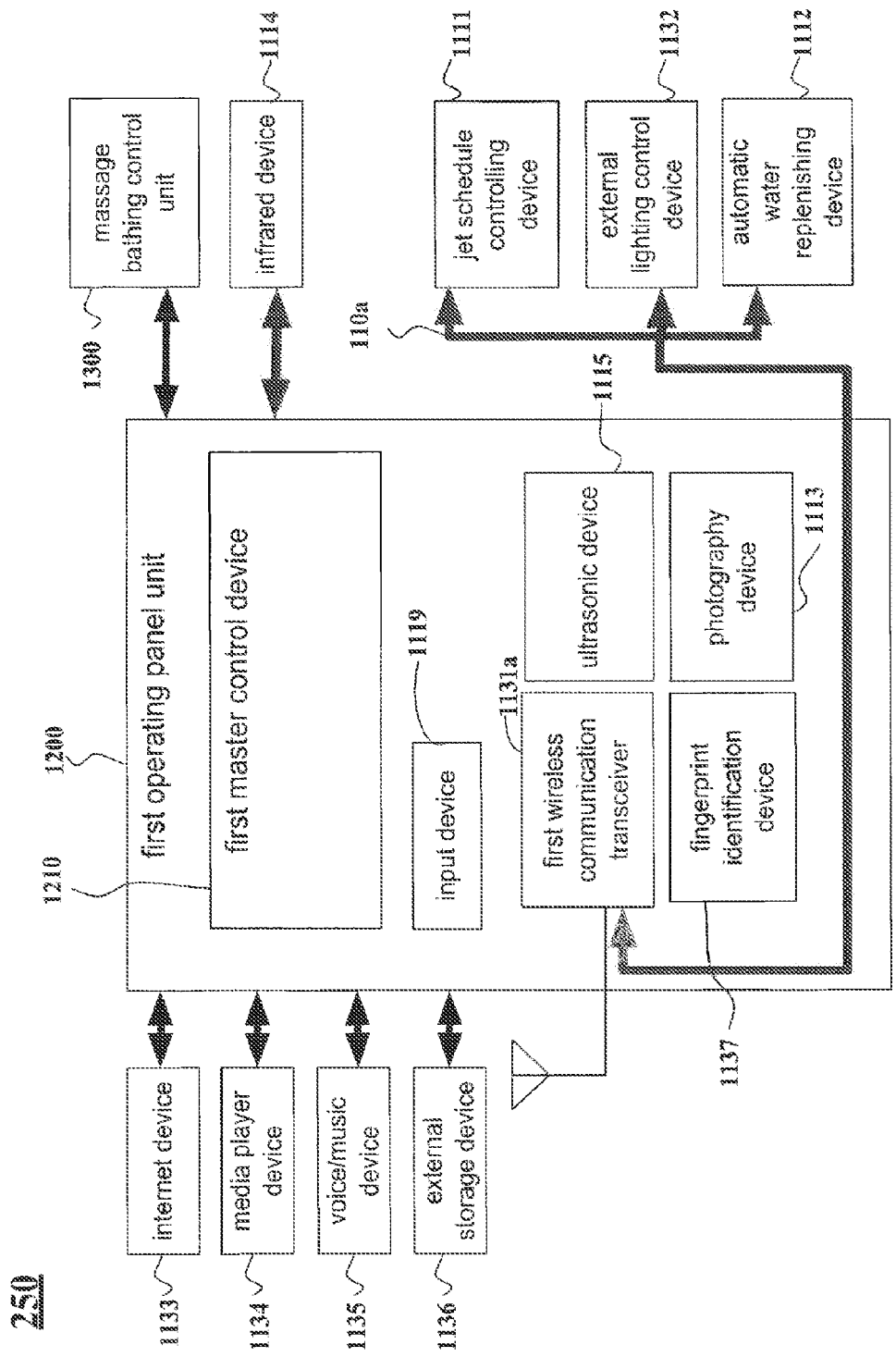
FIG. 22 is an architectural schematic view of the intelligent massage bathing system according to a sixteenth preferred embodiment of the present invention.

Referring to FIG. 22, FIG. 22 is an architectural schematic view of the intelligent massage bathing system 250 according to a sixteenth preferred embodiment of the present invention. The difference between the sixteenth preferred embodiment and the fifteenth preferred embodiment is that: the first operating panel unit 1200 further is connected to an input device 1119. The input device 1119 is a mouse, a keyboard or any device with the same communication protocol as the first master control device 1210.

Figure 23:
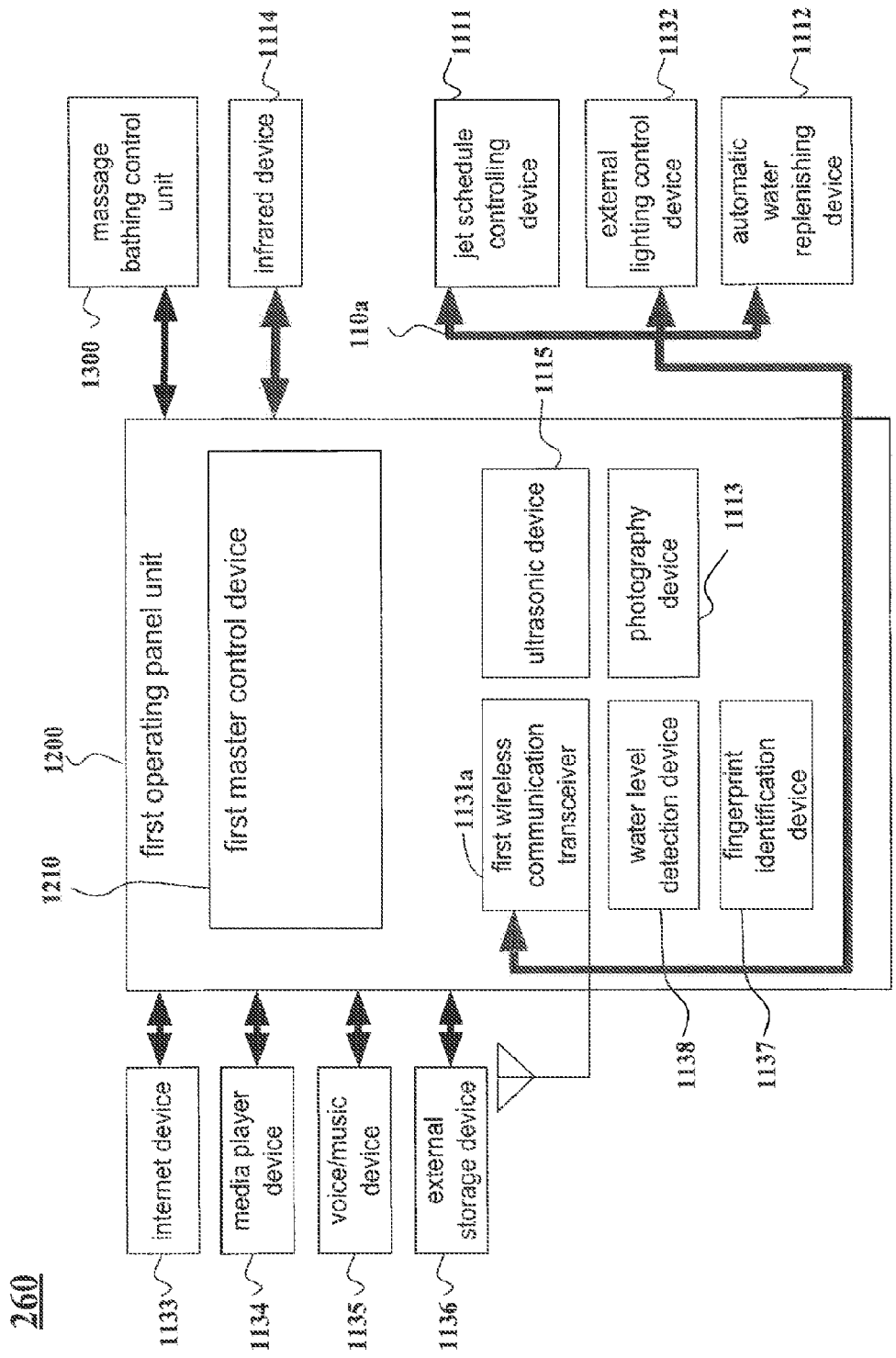
FIG. 23 is an architectural schematic view of the intelligent massage bathing system according to a seventeenth preferred embodiment of the present invention.

Referring to FIG. 23, FIG. 23 is an architectural schematic view of the intelligent massage bathing system 260 according to a seventeenth preferred embodiment of the present invention. The difference between the seventeenth preferred embodiment and the sixteenth preferred embodiment is that: a water level detection device 1138 is integrally assembled with the first operating panel unit 1200 but excludes the input device 1119.

Figure 24:
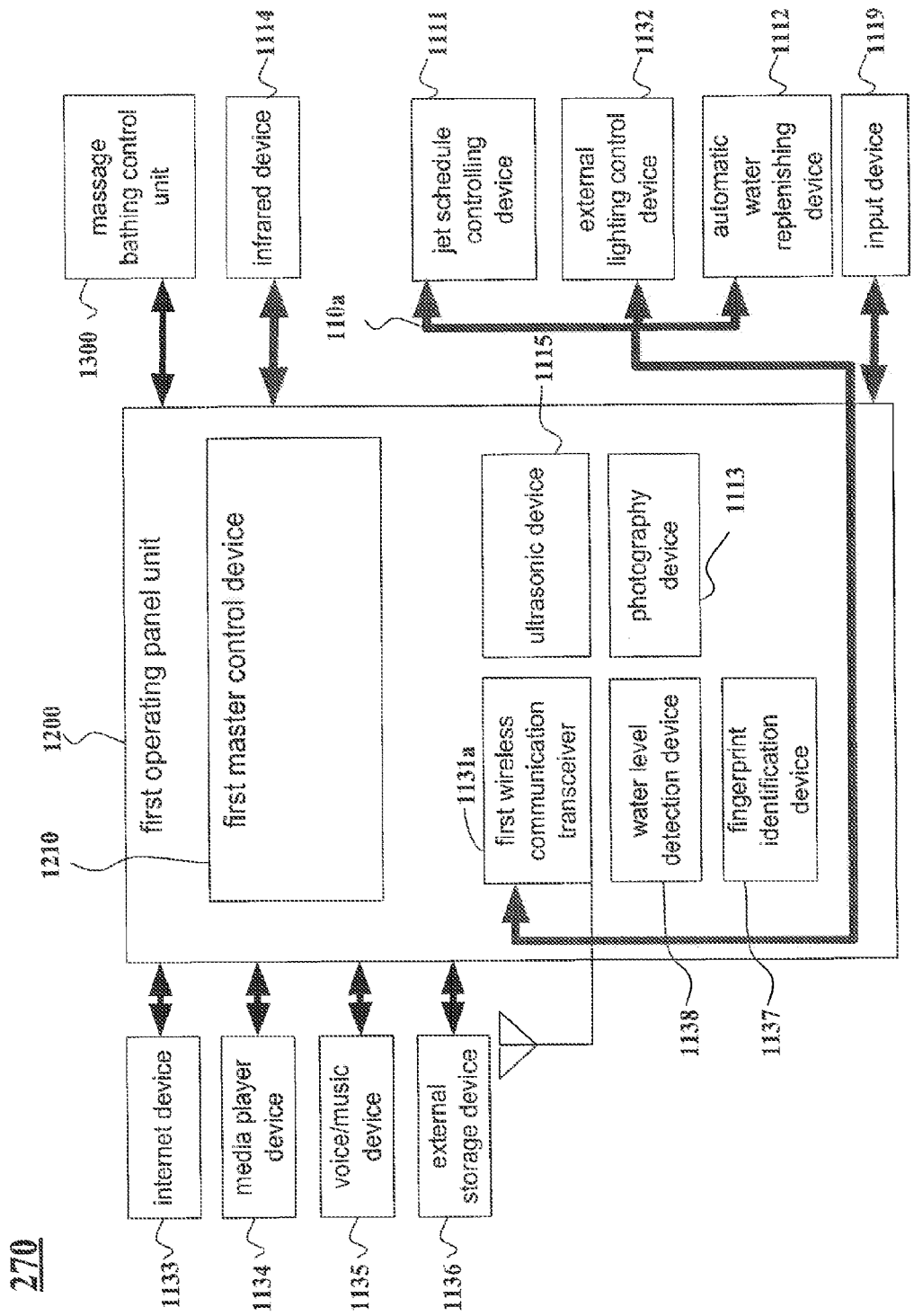
FIG. 24 is an architectural schematic view of the intelligent massage bathing system according to an eighteenth preferred embodiment of the present invention.

Referring to FIG. 24, FIG. 24 is an architectural schematic view of the intelligent massage bathing system 270 according to an eighteenth preferred embodiment of the present invention. The difference between the eighteenth preferred embodiment and the seventeenth preferred embodiment is that: the first operating panel unit 1200 further is connected to an input device 1119. The input device 1119 is a mouse, a keyboard or any device with the same communication protocol as the first master control device 1210.

Figure 25:
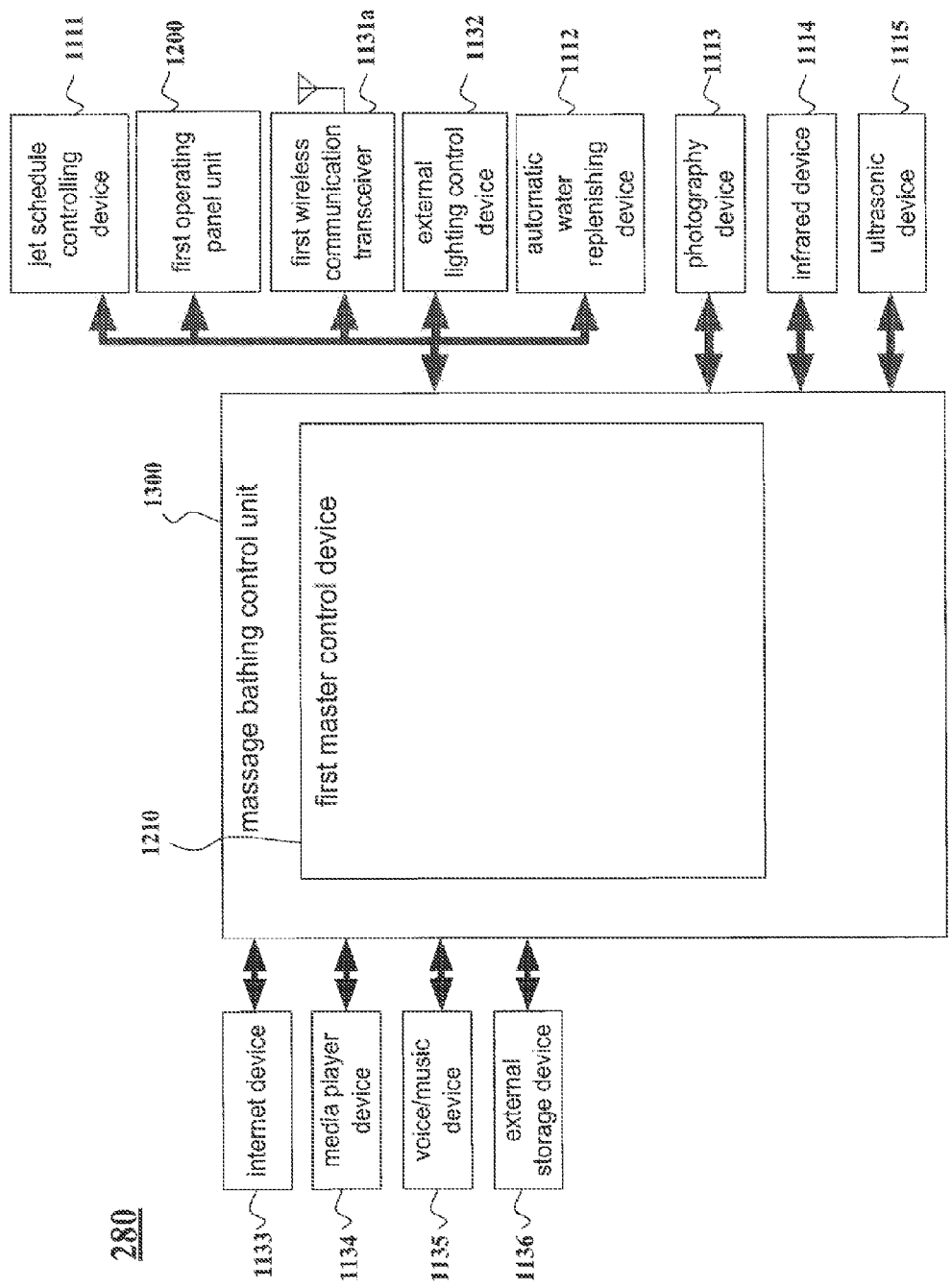
FIG. 25 is an architectural schematic view of the intelligent massage bathing system according to a nineteenth preferred embodiment of the present invention.

Referring to FIG. 25, FIG. 25 is an architectural schematic view of the intelligent massage bathing system 280 according to a nineteenth preferred embodiment of the present invention. The difference between the nineteenth preferred embodiment and the twelfth preferred embodiment is that: the massage bathing control unit 1300 is integrally assembled with the first master control device 1210 and removes the input device 1119. In this embodiment of the present invention, the first operating panel unit 1200 is configured as the second slave control device 1130 shown in FIG. 9.

Figure 26:
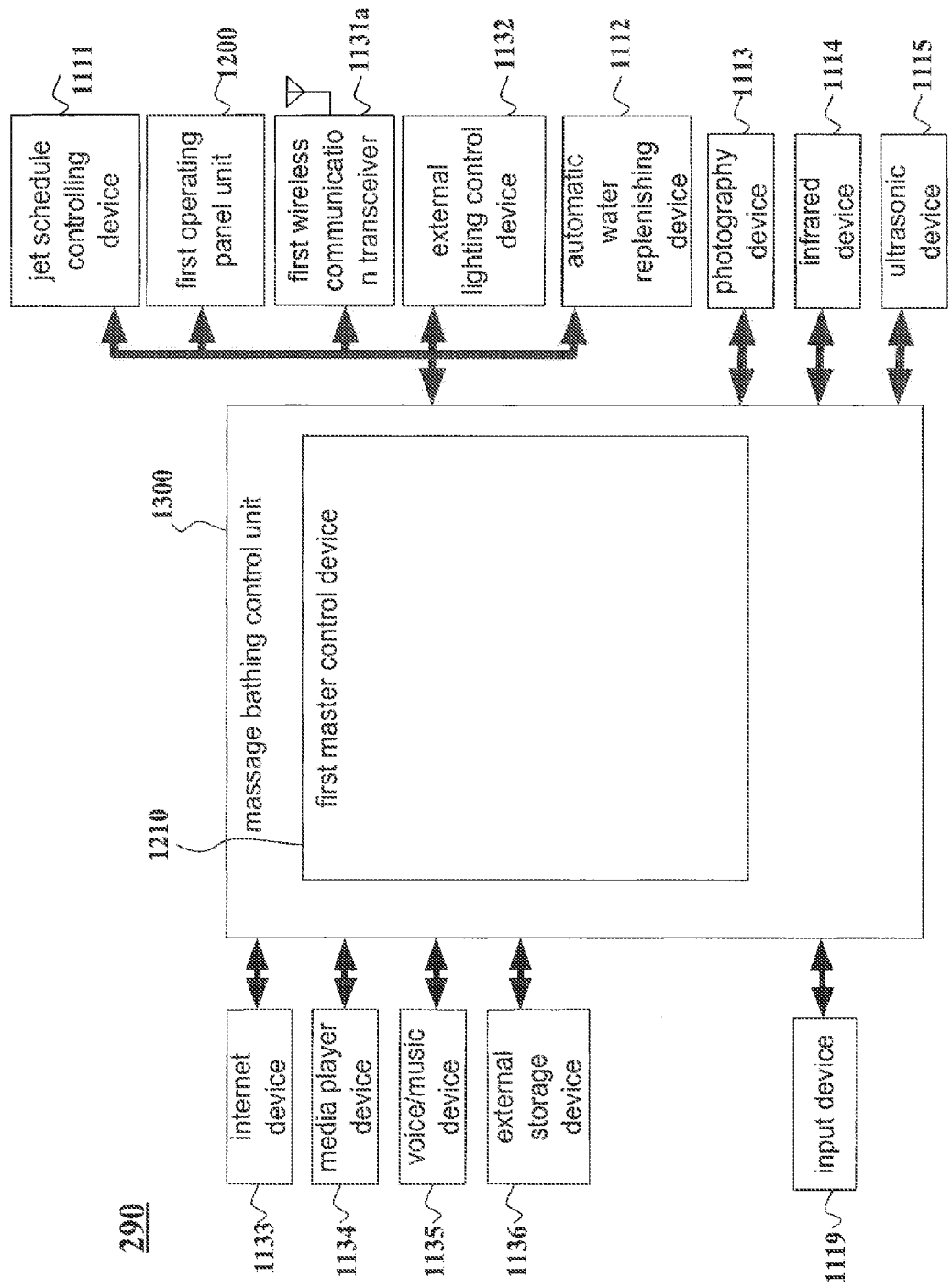
FIG. 26 is an architectural schematic view of the intelligent massage bathing system according to a twentieth preferred embodiment of the present invention.

Referring to FIG. 26, FIG. 26 is an architectural schematic view of the intelligent massage bathing system 290 according to a twentieth preferred embodiment of the present invention. The difference between the twentieth preferred embodiment and the nineteenth preferred embodiment is that: the massage bathing control unit 1300 further is connected to an input device 1119. The input device 1119 is a mouse, a keyboard or any device with the same communication protocol as the first master control device 1210.

Figure 27:
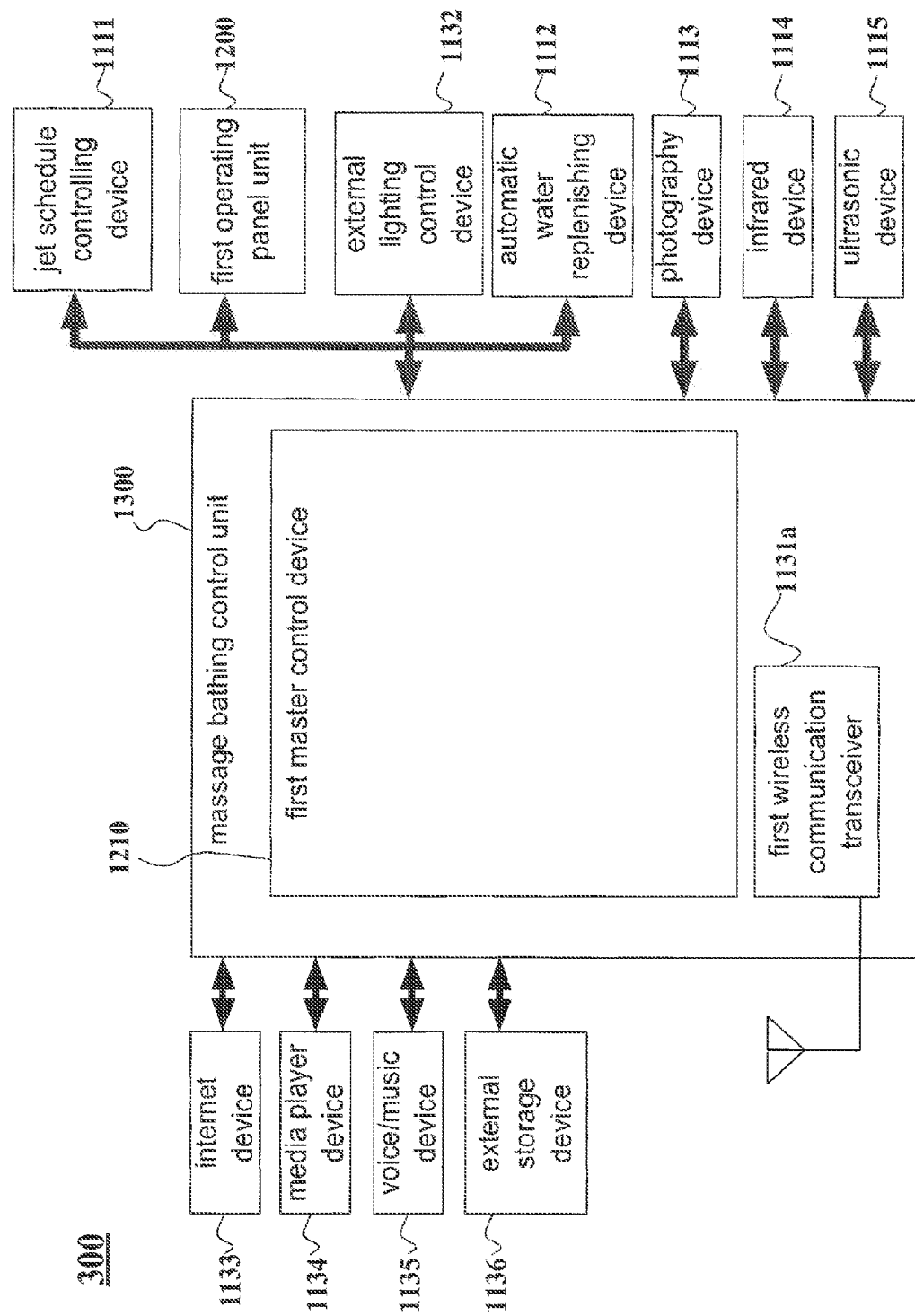
FIG. 27 is an architectural schematic view of the intelligent massage bathing system according to a twenty-first preferred embodiment of the present invention.

Referring to FIG. 27, FIG. 27 is an architectural schematic view of the intelligent massage bathing system 300 according to a twenty-first preferred embodiment of the present invention. The difference between the twenty-first preferred embodiment and the twentieth preferred embodiment is that: the first wireless communication transceiver 1131*a* is integrally assembled with the massage bathing control unit 1300. The first wireless communication transceiver 1131*a* is not disposed within the data bus network architecture.

Figure 28:
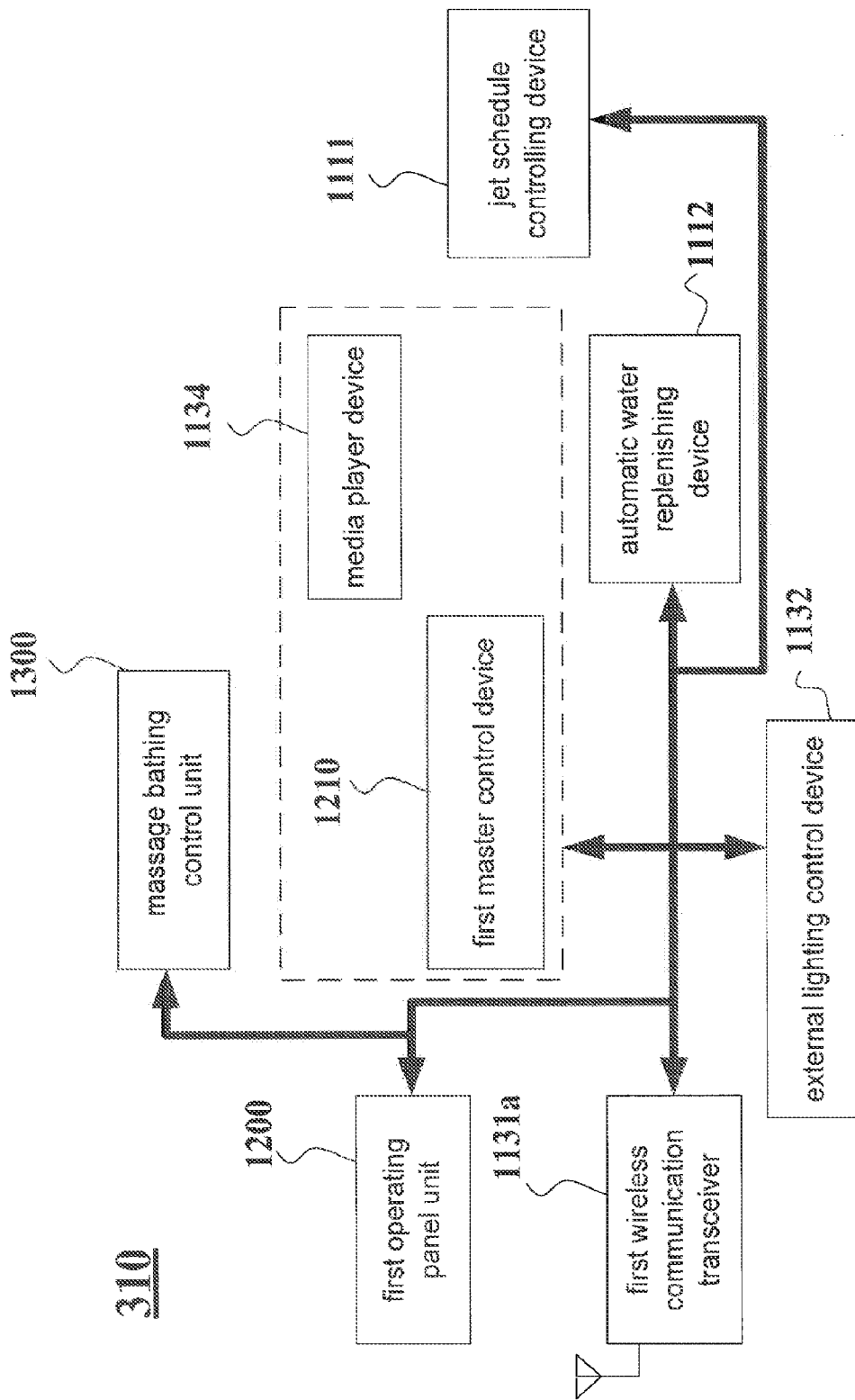
FIG. 28 is an architectural schematic view of the intelligent massage bathing system according to a twenty-second preferred embodiment of the present invention.

Referring to FIG. 28, FIG. 28 is an architectural schematic view of the intelligent massage bathing system 310 according to a twenty-second preferred embodiment of the present invention. The difference between the twenty-second preferred embodiment and the twelfth preferred embodiment is that: the media player device 1134 is integrally assembled with the first master control device 1210. The first operating panel unit 1200 and the massage bathing control unit 1300 are configured as the second slave control device 1130 shown in FIG. 9.

Figure 29:
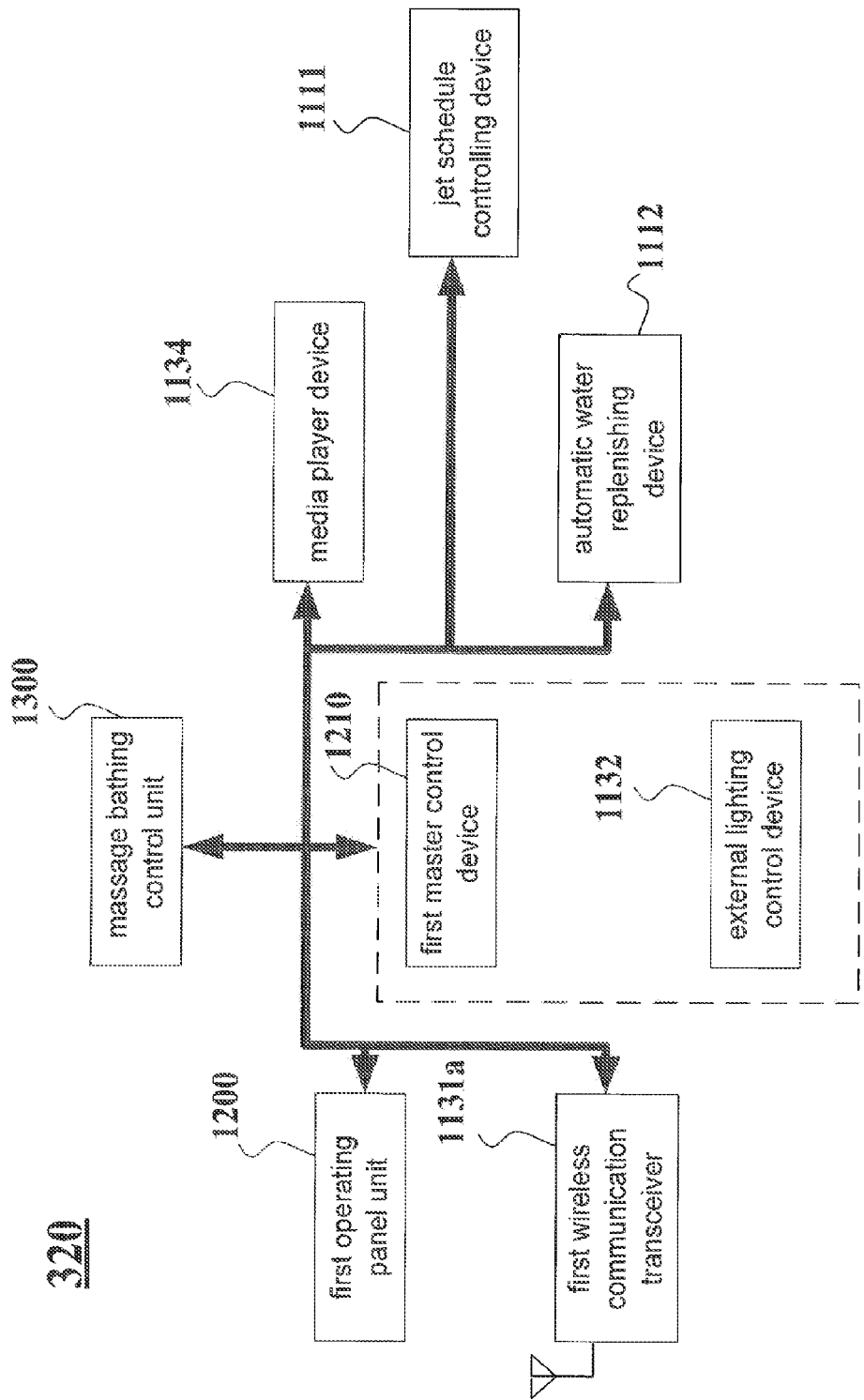
FIG. 29 is an architectural schematic view of the intelligent massage bathing system according to a twenty-third preferred embodiment of the present invention.

Referring to FIG. 29, FIG. 29 is an architectural schematic view of the intelligent massage bathing system 320 according to a twenty-third preferred embodiment of the present invention. The difference between the twenty-third preferred embodiment and the twelfth preferred embodiment is that: the external lighting control device 1132 is integrally assembled with the first master control device 1210. The first operating panel unit 1200 and the massage bathing control unit 1300 are configured as the second slave control device 1130 shown in FIG. 9.

Figure 30:
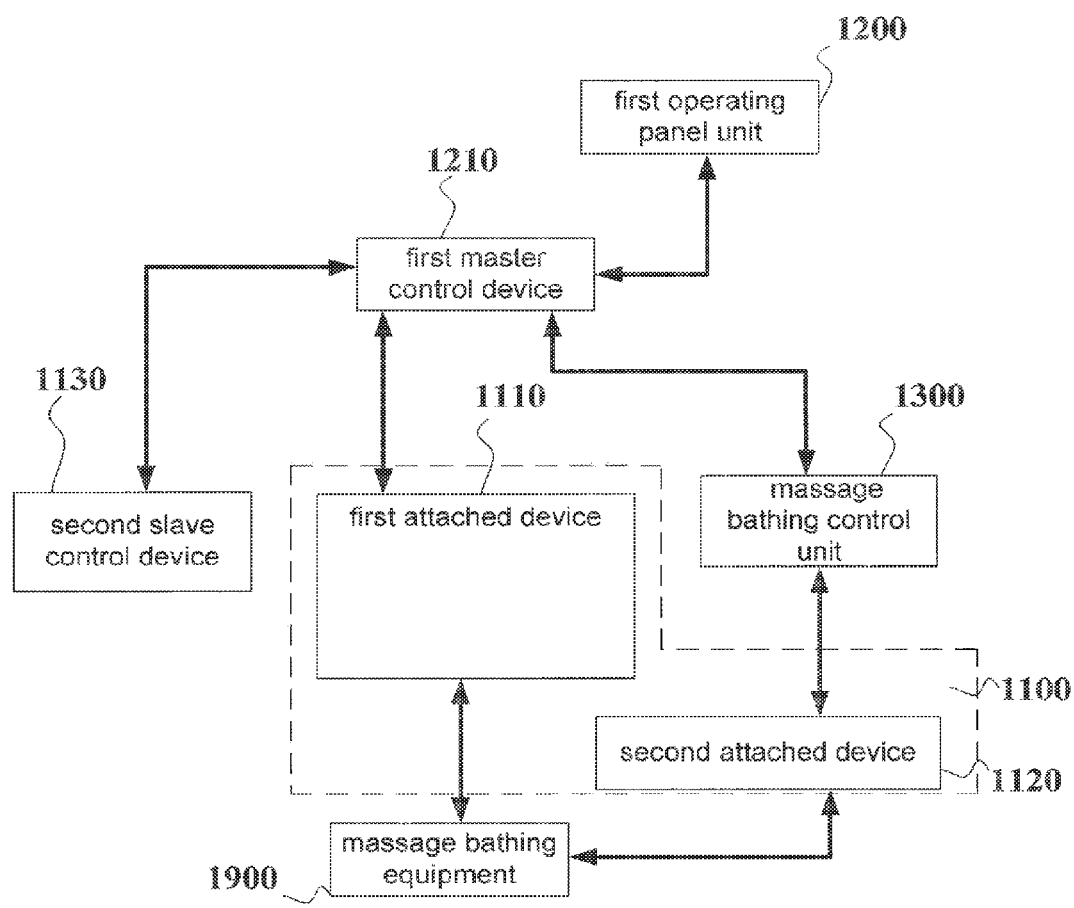
FIG. 30 is an architectural schematic view of the intelligent massage bathing system according to a twenty-fourth preferred embodiment of the present invention.

Referring to FIG. 30, FIG. 30 is an architectural schematic view of the intelligent massage bathing system 330 according to a twenty-fourth preferred embodiment of the present invention. The difference between the twenty-fourth preferred embodiment and the first preferred embodiment is that: all of the first attached devices 1110 of this preferred embodiment cannot be configured as the slave control device.

Referring to FIG. 31, FIG. 31 is a flowchart of a controlling method of the intelligent massage bathing system of the present invention. For the convenience of understanding, please refer to all numerals and the related elements shown in FIGS. 4-30 of the preferred embodiments of the present invention. According to the intelligent massage bathing system of the present invention, the first operating panel unit 1200 can control the attached devices 1100 (including the first slave control device 1140) and the second slave control device 1130 by the first master control device 1210 through the data bus network architecture 110*a*, or can control the attached devices 1100 (including the first slave control device 1140) and the second slave control device 1130 by the second operating panel unit 1500 and the second master control device 1510 through the wireless communication network architecture 110b and the wireless communication transceiver 1131. The controlling method comprises as follows.

In step S01, an instruction is input on a display screen (1202 or 1502) through an input operation module (1201 or 1501) of an operating panel unit (1200 or 1500), the display screen (1202 or 1502) is configured to selectively display an actuated state one or several of the actuated state of the attached devices 1100 relatively to the massage bathing equipment 1900, the attached devices 1100 includes at least one first attached device 1110 and at least one second attached device 1120, wherein the at least one first attached device 1110 is configured as the at least one first slave control device 1140, and the massage bathing control unit 1300 controls an actuation of the at least one second attached device 1120.

Then processing in a step S02, a master control device (1210 or 1510) commands to directly control the at least one first slave control device 1140 by establishing a master-slave connection with the at least one first slave control device 1140, so that the master control device (1210 or 1510) commands to directly control an actuation of the at least one first slave control device 1140 relatively to the massage bathing equipment 1900, according to the instruction from the operating panel unit (1200 or 1500), without control of the massage bathing control unit 1300.

In the step S02, the master control device (1210 or 1510) commands to directly control the at least one second slave control device 1130, 1130' by establishing a master-slave connection with the at least one second slave control device 1130, 1130', without control through the massage bathing control unit 1300, wherein the display screen (1202 or 1502) is configured to selectively display one or several of actuated state of the at least one second slave control device 1130, 1130'.

In the step S02, the second master control device 1510 is connected to the at least one wireless communication transceiver 1131 through the wireless communication network architecture 110b. The at least one second slave control device 1130' comprises at least one wireless communication transceiver 1131.

In the step S02, the first master control device 1210 is respectively connected to a portion of the at least one first slave control device 1140 and/or a portion of the at least one second slave control device 1130, via the data bus network architecture 110a.

In step S02, the second master control device 1510 is connected to the at least one wireless communication transceiver 1131 through the wireless communication network architecture 110b.

In step S02, when the at least one wireless communication transceiver 1131 is connected to the data bus network architecture 110a, the second master control device 1510 commands to directly control an actuation of the corresponding at least one first slave control device 1140 and/or the corresponding second slave control devices 1130, via the at least one wireless communication transceiver 1131, according to the instruction from the second operating panel unit 1500, without control through the massage bathing control unit 1300.

In the step S02, the master control device (1210 or 1510) commands the massage bathing control unit 1300 to control an actuation of the at least one second attached device 1120, according to the instruction from the operating panel unit (1200 or 1500).

In step S02, at least one of the massage bathing control unit 1300 and the first operating panel unit is configured as one of the second slave control devices 1130.

As described above, although the present invention has been described with the preferred embodiments thereof, those skilled in the art will appreciate that various modifications, additions, and substitutions are possible, without departing from the scope and the spirit of the invention. Accordingly, the scope of the present invention is intended to be defined only by reference to the claims.

What is claimed is:

1. An intelligent massage bathing system applied for controlling a massage bathing equipment, in conjunction with a massage bathing control unit, the intelligent massage bathing system comprising:
   at least one slave control modules;
   a plurality of attached devices provided for directly actuating the massage bathing equipment, the attached devices including at least one first attached device and at least one second attached device, the slave control module coupled with the at least one first attached device, wherein the at least one first attached device coupled with the slave control module is configured as at least one first slave control device;
   the massage bathing control unit configured for controlling an actuation of the at least one second attached device;
   a first operating panel unit including a first display screen and a first input operation module for inputting an instruction on the first display screen which is configured to selectively display an actuated state of one or a combination of several of the at least one first attached device and the at least one first slave control device;
   a first master control device coupled with the massage bathing control unit, for electrically connecting with the first operating panel unit and for directly controlling, through establishing a master-slave connection, on the at least one first slave control device and the at least one first attached device, wherein the first master control device directly controls the at least one first slave control device and the at least one first attached device, according to the instruction from the first operating panel unit, and wherein the first master control device further including a plurality of drive control components and a multitasking kernel for directly controlling the at least one first attached device and the at least one first slave control device without controlling of the massage bathing control unit; and
   a plurality of second slave control devices, each of the second slave control devices respectively establishes a master-slave connection with the first master control device so as to actuate through direct control of the first master control device without controlling of the massage bathing control unit;
   wherein at least one second slave control devices further comprises at least one wireless communication transceiver, the wireless communication transceiver electrically connected to the first master control device, for the first master control device receiving the instruction;
   wherein the first master control device commands one or several of actuation of the at least one second attached device controlled through the massage bathing control unit;
   wherein the first master control device controls the massage bathing control unit to control one or several actuations of the at least one second attached device;

wherein the first master control device directly controls one or several actuations of the massage bathing control unit.

2. The massage bathing system according to claim 1, wherein the at least one first attached device comprises one or a combination of several of a jet schedule controlling device, an automatic water replenishing device, an infrared device, a photography device and an ultrasonic device, and the at least one second attached device comprises one or a combination of several of a blower, a motor, an air valve, a sensor, a pump, an internal light controlling device and a heater.

3. The massage bathing system according, to claim 1, wherein the first display screen being configured to selectively display an actuated state of one or a combination of several of the attached devices and the second slave control devices.

4. The massage bathing system according to claim 3, wherein the second slave control devices comprises one or a combination of several of an external lighting control device, a media player device, an internet device, an external storage device and a voice/music device.

5. The massage bathing system according to claim 4, wherein the at least one wireless communication transceiver comprises at least one first wireless communication transceiver.

6. The massage bathing system according to claim 5 further comprising a data bus network architecture which comprises a first region master node and a plurality of first region slave nodes for electrically connecting with the first region master node, wherein a portion of the at least one first slave control device and/or a portion of the second slave control devices are respectively disposed on the first region slave nodes, the first master control device is disposed on the first region master node.

7. The massage bathing system according to claim 6, wherein the first wireless communication transceiver is disposed on the corresponding first region slave node.

8. The massage bathing system according to claim 6, wherein the data bus network architecture comprises one or a combination of several of RS-485, CAN Bus and LIN Bus.

9. The massage bathing system according to claim 6 or 7 further comprising:
  a wireless communication network architecture which comprises a second region master node and at least one second region slave node for connecting with the second region master node;
  a second operating panel unit including a second display screen and a second input operation module for inputting an instruction on the second display screen, and the second display screen being configured to selectively display an actuated state of one or a combination of several of the attached devices and the second slave control devices; and
  a second master control device disposed on the second region master node and electrically connecting with the second operating panel unit, wherein the first wireless communication transceiver is disposed on the at least one second region slave node.

10. The massage bathing system according to claim 9, wherein the second master control device further commands one or several of actuation of the at least one second attached device controlled through the massage bathing control unit, actuation of the at least one first slave control device and actuations of the other second slave control devices, via the first wireless communication transceiver, according to the instruction from the second operating panel unit.

11. The massage bathing system according to claim 9, wherein the at least one wireless communication transceiver further comprises at least one second wireless communication transceiver which comprises one or a combination of several of a Zigbee transceiver, a RF transceiver and a Bluetooth transceiver.

12. The massage bathing system according to claim 11, wherein the second wireless communication transceiver is disposed on the corresponding first region slave node.

13. The massage bathing system according to claim 11, wherein the second master control device further commands one or several of actuation of the at least one second attached device controlled through the massage bathing control unit and actuations of the other second slave control devices, via the first wireless communication transceiver and the second wireless communication transceiver, according to the instruction from the second operating panel unit.

14. The massage bathing system according to claim 11, wherein the first master control device commands actuations of the other at least one second slave control devices, via the second wireless communication transceiver, according to the instruction from the first operating panel unit.

15. The massage bathing system according to claim 3, wherein the at least one of the massage bathing control unit and the first operating panel unit are configured as one of the second slave control devices.

16. The massage bathing system according to claim 1, wherein one of the massage bathing control unit and the first operating panel unit is integrally assembled with the first master control device.

17. The massage bathing system according to claim 3, wherein one of the at least one first attached device and the at least one second slave control device is integrally assembled with the first master control device.

18. The massage bathing system according to claim 3, wherein the first master control device comprises a memory unit, a network communication interface unit, a general asynchronous transceiver unit and a microprocessor unit, wherein the microprocessor unit comprises a plurality of drive control components and a multitasking kernel, the drive control components are configured to process a direct control, through a master-slave connection, on the at least one first slave control device and a plurality of second slave control devices.

19. The massage bathing system according to claim 18, wherein the multitasking kernel comprises multi-threads.

20. The massage bathing system according to claim 18, wherein the first master control device further comprises an image processing unit, an voice processing unit, an information collection unit, an output controlling unit, a USB interface and a power management unit.

21. The massage bathing system according to claim 1, wherein the at least one first slave control device further comprises a slave control module.

22. A controlling method of a massage bathing system applied for controlling a massage bathing equipment, the massage bathing equipment further controlled by a massage bathing control unit, the controlling method comprising:
  inputting an instruction on a display screen through an input operation module of an operating panel unit, wherein the display screen is configured to selectively display an actuated state of one or a combination of several of attached devices actuating the massage bathing equipment, and wherein the massage bathing system includes at least one slave control modules, the attached devices includes at least one first attached device and at least one second attached device, the slave control module coupled with the at least one first attached device, wherein the at least one first attached device coupled with the slave control module is configured as at least one first slave control device, and the at least one second attached device is controlled to actuate by the massage bathing control unit; and configuring a master control device to directly control, through establishing a master-slave connection, on the at least one first slave control device and the at least one first attached device, and to directly control an actuation of the at least one first slave control device and the at least one first attached device actuating the massage bathing equipment without controlling of the massage bathing control unit, according to the instruction from the operating panel unit; and the master control device commanding one or several of actuation of the at least one second attached device controlled through the massage bathing control unit;

wherein the master control device controls the massage bathing control unit to control one or several of actuation of the at least one second attached device;

wherein the master control device directly controls one or several of actuation of the massage bathing control unit.

23. The controlling method of the massage bathing system according to claim 22, further comprising: configuring the master control device to process a direct control, through the master-slave connection, on at least one second slave control device, wherein the display screen is configured to selectively display one or several of actuated state of the at least one second slave control device.

24. The controlling method of the massage bathing system according to claim 23, wherein the at least one second slave control device comprises at least one wireless communication transceiver.

25. The controlling method of the massage bathing system according to claim 24 further comprising: the master control device being respectively connected to a portion of the at least one first slave control device and/or a portion of the at least one second slave control device via a data bus network architecture.

26. The controlling method of the massage bathing system according to claim 24 or 25 further comprising: configuring the master control device to be connected to the at least one wireless communication transceiver via a wireless communication network architecture.

27. The controlling method of the massage bathing system according to claim 26, wherein when the at least one wireless communication transceiver is connected to the data bus network architecture, the master control device commands to directly control an actuation of the corresponding at least one first slave control device and/or the corresponding at least one second slave control device, via the at least one wireless communication transceiver, according to the instruction from the operating panel unit.

28. The controlling method of the massage bathing system according to claim 23 further comprising: the master control device commanding actuation of the at least one first slave control device and actuations of the at least one second slave control devices, according to the instruction from the operating panel unit.

29. The controlling method of the massage bathing system according to claim 23, wherein the at least one of the massage bathing control unit and the operating panel unit are configured as one of the at least one second slave control device.

30. The controlling method of the massage bathing system according to claim 25, wherein the data bus network architecture comprises one or a combination of several of RS-485, CAN Bus and LIN Bus.

31. The massage bathing system according to claim 5, wherein the at least one wireless communication transceiver comprises one or a combination of several of a Wi-Fi transceiver, a Zigbee transceiver, a RF transceiver and a Bluetooth transceiver.

32. The massage bathing system according to claim 17, wherein the first master control device comprises at least one wireless communication transceiver, and the at least one wireless communication transceiver comprises one or a combination of several of a Wi-Fi transceiver, a Zigbee transceiver, a RP transceiver and a Bluetooth transceiver.

* * * * *